(12) United States Patent
Baumgartner

(10) Patent No.: US 10,640,460 B2
(45) Date of Patent: May 5, 2020

(54) SUBSTITUTED CYCLOPENTYL- AND CYCLOHEXYL-DERIVATIVES USEFUL FOR PERFUMERY

(71) Applicant: Givaudan, S.A., Vernier (CH)

(72) Inventor: Corinne Baumgartner, Fällanden (CH)

(73) Assignee: Givaudan SA, Vernier (CH)

(*) Notice: Subject to any disclaimer, the term of this patent is extended or adjusted under 35 U.S.C. 154(b) by 129 days.

(21) Appl. No.: 15/779,982

(22) PCT Filed: Dec. 8, 2016

(86) PCT No.: PCT/EP2016/080219
§ 371 (c)(1),
(2) Date: May 30, 2018

(87) PCT Pub. No.: WO2017/097884
PCT Pub. Date: Jun. 15, 2017

(65) Prior Publication Data
US 2018/0346412 A1 Dec. 6, 2018

(30) Foreign Application Priority Data

Dec. 10, 2015 (GB) .................................. 1521758.1

(51) Int. Cl.
*C11B 9/00* (2006.01)
*C07C 255/00* (2006.01)
*C07C 255/31* (2006.01)
*C07C 69/608* (2006.01)

(52) U.S. Cl.
CPC .......... *C07C 255/31* (2013.01); *C07C 69/608* (2013.01); *C11B 9/003* (2013.01); *C11B 9/0019* (2013.01); *C11B 9/0023* (2013.01); *C11B 9/0034* (2013.01); *C07C 2601/08* (2017.05); *C07C 2601/14* (2017.05); *C07C 2602/50* (2017.05)

(58) Field of Classification Search
CPC ..... C11B 9/0019; C11B 9/0023; C11B 9/003; C11B 9/0034; C07C 69/608; C07C 255/31; C07C 26/01
See application file for complete search history.

(56) References Cited

U.S. PATENT DOCUMENTS

| | | | |
|---|---|---|---|
| 4,912,088 | A | 3/1990 | Brunke et al. |
| 5,049,544 | A | 9/1991 | Koshino et al. |
| 5,164,364 | A | 11/1992 | Rohr et al. |
| 7,361,630 | B2 | 4/2008 | Narula et al. |
| 9,012,391 | B2 | 4/2015 | Granier et al. |
| 2007/0055082 | A1 | 3/2007 | Narula et al. |
| 2010/0292128 | A1 | 11/2010 | Granier et al. |

FOREIGN PATENT DOCUMENTS

| | | |
|---|---|---|
| EP | 0 302 816 A2 | 2/1989 |
| EP | 0 411 460 A1 | 2/1991 |
| EP | 1 182 190 A1 | 2/2002 |
| EP | 1 752 565 A1 | 3/2007 |
| WO | WO 2008/151455 A1 | 12/2008 |

OTHER PUBLICATIONS

PCT/EP2016/080219—International Search Report, dated Feb. 8, 2017.
PCT/EP2016/080219—International Written Opinion, dated Feb. 8, 2017.
Julian C. Lo, et al., "A Practical and Catalytic Reductive Olefin Coupling", Journal of the American Chemical Society, Jan. 15, 2014, pp. 1304-1307, Issue 136.

*Primary Examiner* — Caixia Lu
(74) *Attorney, Agent, or Firm* — Curatolo Sidoti Co., LPA; Joseph G. Curatolo; Salvatore A. Sidoti

(57) ABSTRACT

The present invention refers to substituted cyclopentyl- and cyclohexyl-derivatives of formula (I)

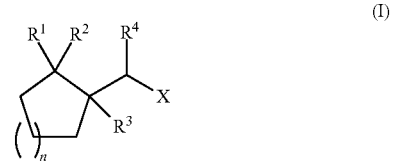

wherein n, $R^1$, $R^2$, $R^3$, $R^4$ and X have the same meaning as given in the description.
The invention further refers to fragrance compositions and fragranced articles comprising them.

7 Claims, No Drawings

SUBSTITUTED CYCLOPENTYL- AND CYCLOHEXYL-DERIVATIVES USEFUL FOR PERFUMERY

CROSS REFERENCE TO RELATED APPLICATIONS

This application is a national stage application of International Application No. PCT/EP2016/080219, filed 8 Dec. 2016, which claims priority from Great Britain Patent Application No. 1521758.1, filed 10 Dec. 2015, which applications are incorporated herein by reference.

The present invention relates to substituted cyclopentyl- and cyclohexyl-derivatives possessing odor notes useful for perfumery, which are in the fruity range. This invention relates furthermore to flavor and fragrance compositions and flavored or fragranced articles comprising them.

In the fragrance industry there is a constant demand for new compounds that enhance, modify or improve on odor notes. Surprisingly, it has now been found that certain cyclopentyl- and cyclohexyl derivatives of formula (I) as defined below constitute valuable fruity odorants, for example, fruity odorants reminiscent of red fruits and/or apple, further possessing agrestic connotations.

Accordingly, the present invention refers in one of its aspects to the use as flavor or fragrance of a compound of formula (I), or a mixture thereof

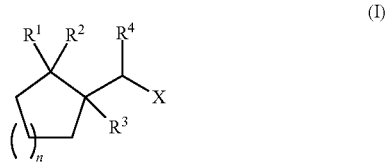

(I)

wherein
n is 1 or 2;
$R^1$ and $R^2$ are independently selected from hydrogen, methyl, ethyl, and $C_3$-$C_5$ alkyl ((linear or branched), such as propyl, isopropyl, tert-butyl, 1-methylpropyl, isobutyl, and isopentyl);
or
$R^1$ and $R^2$ form together with the carbon atom to which they are attached $C_3$-$C_6$ cycloalkyl (e.g., cyclopentyl);
or
$R^1$ and $R^2$ form together methylidene;
$R^3$ is selected from hydrogen, $C_1$-$C_3$ alkyl (e.g. ethyl, propyl, isopropyl);
$R^4$ is selected from hydrogen, and $C_1$-$C_3$ alkyl (e.g. ethyl, propyl, isopropyl); and
X is —CN; or
X is —C(O)OR$^5$, wherein $R^5$ is selected from methyl, ethyl, $C_3$-$C_5$ alkyl ((linear or branched), such as propyl, isopropyl, tert-butyl, 1-methylpropyl, isobutyl, and isopentyl), vinyl and $C_3$-$C_5$ alkenyl ((linear or branched), such as 2-methylprop-2-en-1-yl, prop-2-en-1-yl, 3-methyl-but-2-enyl, and but-3-en-1-yl);
with the proviso that
  a) at least two of the residues $R^1$, $R^2$ and $R^3$ are not hydrogen;
  b) when $R^3$ is hydrogen, $R^4$ is selected from $C_1$-$C_3$ alkyl;
  c) when X is —CN, and $R^1$, $R^2$ and $R^3$ are methyl, then $R^4$ is not hydrogen.

Non-limiting examples are compounds of formula (I) wherein $R^3$ and $R^4$ are not hydrogen.

Further, non-limiting examples are compounds of formula (I) wherein $R^1$, $R^3$ and $R^4$ are not hydrogen.

Further, non-limiting examples are compounds of formula (I) wherein $R^3$ is methyl or ethyl and $R^4$ is selected from methyl, ethyl, propyl and isopropyl.

Further, non-limiting examples are compounds of formula (I) wherein n is 2, $R^1$ and $R^2$ are not hydrogen, and either $R^3$ or $R^4$ is not hydrogen.

Further, non-limiting examples are compounds of formula (I) wherein $R^1$ is hydrogen and $R^2$ is selected from methyl, ethyl, and linear or branched $C_3$-$C_5$ alkyl (e.g., propyl, isopropyl, tert-butyl, 1-methylpropyl, isobutyl, and isopentyl).

Further, non-limiting examples are compounds of formula (I) wherein $R^1$, $R^2$, $R^3$ and $R^4$ are methyl, and X is —CN or C(O)OR$^5$, wherein $R^5$ is selected from methyl, ethyl, $C_3$-$C_5$ alkyl ((linear or branched), such as propyl, isopropyl, tert-butyl, 1-methylpropyl, isobutyl, and isopentyl), vinyl and $C_3$-$C_5$ alkenyl ((linear or branched), such as 2-methylprop-2-en-1-yl, prop-2-en-1-yl, and 3-methyl-but-2-enyl, but-3-en-1-yl).

Further, non-limiting examples are compounds of formula (I) wherein X is —CN, $R^3$ is methyl, and $R^4$ is selected from hydrogen, methyl, ethyl, propyl and isopropyl.

Further, non-limiting examples are compounds of formula (I) wherein X is —CN, $R^3$ is methyl, $R^1$ is hydrogen or methyl, and $R^2$ is selected from methyl, ethyl, and linear or branched $C_3$-$C_5$ alkyl.

Further, non-limiting examples are compounds of formula (I) wherein X is —CN, $R^1$ is methyl, $R^2$ is hydrogen, methyl or ethyl, $R^3$ is methyl, and $R^4$ is selected from hydrogen, and $C_1$-$C_3$ alkyl (e.g. ethyl, propyl, isopropyl).

Further, non-limiting examples are compounds of formula (I) wherein X is —C(O)OR$^5$ and wherein $R^5$ is selected from methyl, ethyl, $C_3$-$C_5$ alkyl ((linear or branched), such as propyl, isopropyl, tert-butyl, 1-methylpropyl, isobutyl, and isopentyl), vinyl and $C_3$-$C_5$ alkenyl ((linear or branched), such as 2-methylprop-2-en-1-yl, prop-2-en-1-yl, and 3-methyl-but-2-enyl, but-3-en-1-yl), $R^3$ is methyl, and $R^1$ and $R^2$ form together with the carbon atom to which they are attached a 5 membered hydrocarbon ring (e.g. cyclopentyl).

Further, non-limiting examples are compounds of formula (I) wherein X is —C(O)OR$^5$ and wherein $R^5$ is selected from methyl, ethyl, $C_3$-$C_5$ alkyl ((linear or branched), such as propyl, isopropyl, tert-butyl, 1-methylpropyl, isobutyl, and isopentyl), vinyl and $C_3$-$C_5$ alkenyl ((linear or branched), such as 2-methylprop-2-en-1-yl, prop-2-en-1-yl, and 3-methyl-but-2-enyl, but-3-en-1-yl), $R^3$ is methyl, and $R^4$ is selected from hydrogen, methyl, ethyl, propyl and isopropyl.

Further, non-limiting examples are compounds of formula (I) wherein X is —C(O)OR$^5$ and wherein $R^5$ is selected from methyl, ethyl, $C_3$-$C_5$ alkyl ((linear or branched), such as propyl, isopropyl, tert-butyl, 1-methylpropyl, isobutyl, and isopentyl), vinyl and $C_3$-$C_5$ alkenyl ((linear or branched), such as 2-methylprop-2-en-1-yl, prop-2-en-1-yl, and 3-methyl-but-2-enyl, but-3-en-1-yl), $R^3$ is methyl, $R^1$ is hydrogen or methyl, and $R^2$ is selected from methyl, ethyl, and linear or branched $C_3$-$C_5$ alkyl.

As a specific example of compounds of formula (I), one may cite, as non-limiting example, ethyl 2-(1,2,2-trimethylcyclopentyl)propanoate), which possesses a distinct fruity, agrestic odor with strawberry and apple connotations.

Further, non-limiting examples are compounds of formula (I) selected from
methyl 2-(1,2,2-trimethylcyclopentyl)acetate (Ex2a),
methyl 2-(1,2,2-trimethylcyclopentyl)propanoate (Ex2b),
propyl 2-(1,2,2-trimethylcyclopentyl)propanoate (Ex 3b), isopropyl 2-(1,2,2-trimethylcyclopentyl)propanoate (Ex 3c),
but-3-en-1-yl 2-(1,2,2-trimethylcyclopentyl)propanoate (Ex 3d),
isobutyl 2-(1,2,2-trimethylcyclopentyl)propanoate (Ex 3e),
allyl 2-(1,2,2-trimethylcyclopentyl)propanoate (Ex 3f),
methyl 2-(1-methylspiro[4.4]nonan-1-yl)acetate (Ex 4a),
methyl 2-(1-methylspiro[4.4]nonan-1-yl)propanoate (Ex 4b),
ethyl 2-(1-methylspiro[4.4]nonan-1-yl)acetate (Ex 4c),
ethyl 2-(1-methylspiro[4.4]nonan-1-yl)propanoate (Ex 4d),
ethyl 2-(1-methyl-2-methylenecyclopentyl)propanoate (Ex 5a),
ethyl 2-(4-methylspiro[2.4]heptan-4-yl)propanoate (Ex 5b),
ethyl 2-(2-ethyl-1,2-dimethylcyclopentyl)acetate (Ex 6b),
ethyl 2-(2-ethyl-1,2-dimethylcyclopentyl)propanoate (Ex 6c),
ethyl 2-(1,2-dimethyl-2-propylcyclopentyl)propanoate (Ex 6e),
ethyl 2-(1,2,2-trimethylcyclopentyl)acetate (Ex 7a),
ethyl 2-(1,2,2-trimethylcyclopentyl)butanoate (Ex 7b),
ethyl 2-(1,2,2-trimethylcyclopentyl)pentanoate (Ex 7c),
ethyl 2-(1-ethyl-2,2-dimethylcyclopentyl)propanoate (Ex 8),
ethyl 2-(1,2-dimethylcyclopentyl)propanoate (Ex 9),
2-(1,2,2-trimethylcyclopentyl)propanenitrile (Ex 10b),
2-(2-ethyl-1,2-dimethylcyclopentyl)acetonitrile (Ex 10d),
ethyl 2-(2,2-dimethylcyclopentyl)propanoate (Ex 11a/c),
ethyl 2-(2,2-dimethylcyclohexyl)propanoate (Ex 12a),
ethyl 2-(1,2,2-trimethylcyclohexyl)acetate (Ex 12b), and
ethyl 2-(1,2,2-trimethylcyclohexyl)propanoate (Ex 12c).

The compound of formula (I) may be used alone, as stereoisomeric mixture, or in combination with a base material. As used herein, the 'base material' includes all known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the art.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

The following list comprises examples of known odorant molecules, which may be combined with the compound of the present invention:
  essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
  alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-01); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
  aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl)ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;
  ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2%2%3,7,7-pentamethylspiro[bicyclo[4.1.0]heptane-2,5'-[1,3]dioxane]);
  esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl)acetate);
  macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

The compound according to formula (I) may be used in a broad range of fragranced articles, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 30 weight percent of the article. In one embodiment, the compound of the present invention may be employed in a fabric softener in an amount from 0.001 to 0.3 weight percent. In another embodiment, the compound of the present invention may be used in fine perfumery in amounts from 0.01 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

The compound as described hereinabove may be employed in a consumer product base simply by directly mixing the compound of formula (I), or a fragrance composition with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release the fragrance molecule upon application of an external stimulus such as light, enzyme, oxygen, or the like, and then mixed with the consumer product base.

Thus, the invention additionally provides a method of manufacturing a fragranced article, comprising the incorporation of a compound of formula (I), as a fragrance ingredient, either by directly admixing the compound to the consumer product base or by admixing a fragrance composition comprising the compound of formula (I), which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I).

The invention also provides a fragranced article comprising:
a) as odorant the compound of formula (I), or a mixture thereof; and
b) a consumer product base.

As used herein, 'consumer product base' means a composition for use as a consumer product to fulfil specific actions, such as cleaning, softening, and caring or the like.

Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, *eucalyptus* oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Cosmetic products include:
(a) cosmetic skincare products, especially bath products, skin washing and cleansing products, skincare products, eye makeup, lip care products, nail care products, intimate care products, foot care products;
(b) cosmetic products with specific effects, especially sunscreens, tanning products, de-pigmenting products, deodorants, antiperspirants, hair removers, and shaving products;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

This list of products is given by way of illustration, and is not to be regarded as being in any way limiting.

Whereas, according to our best knowledge, only very few compounds as such are known from the literature, other compounds falling within the definition of formula (I) as hereinabove defined are not described in the literature and are thus novel in their own right.

Thus, there is provided in a further aspect of the invention a compound of formula (I)

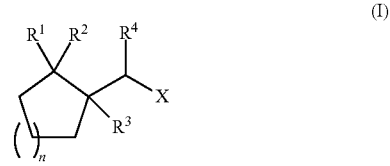

(I)

wherein
n is 1 or 2;
$R^1$ and $R^2$ are independently selected from hydrogen, methyl, ethyl, and $C_3$-$C_5$ alkyl ((linear or branched), such as propyl, isopropyl, tert-butyl, 1-methylpropyl, isobutyl, and isopentyl);
or
$R^1$ and $R^2$ form together with the carbon atom to which they are attached $C_3$-$C_6$ cycloalkyl (e.g., cyclopentyl);
$R^3$ is selected from hydrogen, $C_1$-$C_3$ alkyl (e.g. ethyl, propyl, isopropyl);
$R^4$ is selected from hydrogen, and $C_1$-$C_3$ alkyl (e.g. ethyl, propyl, isopropyl); and
X is —CN; or
X is —C(O)OR$^5$, wherein R$^5$ is selected from methyl, ethyl, $C_3$-$C_5$ alkyl ((linear or branched), such as propyl, isopropyl, tert-butyl, 1-methylpropyl, isobutyl, and isopentyl), vinyl and $C_3$-$C_5$ alkenyl ((linear or branched), such as 2-methylprop-2-en-1-yl, prop-2-en-1-yl, 3-methyl-but-2-enyl, and but-3-en-1-yl);
with the proviso that
a) at least two of the residues $R^1$, $R^2$ and $R^3$ is not hydrogen;
b) when $R^3$ is hydrogen, $R^4$ is selected from $C_1$-$C_3$ alkyl;
c) when X is —CN, and $R^1$, $R^2$ and $R^3$ are methyl, then $R^4$ is not hydrogen;
d) when n is 2, then $R^1$ and $R^2$ are not hydrogen.

The compounds of formula (I) give rise to a number of stereoisomers, and can be resolved into individual enriched or pure enantiomers or diastereomers. Resolving stereoisomers however adds to the complexity of manufacture and purification of these compounds, as does a stereoselective synthetic approach, and thus it is preferred to use the compounds as mixtures of their stereoisomers simply for economic reasons. However, if it is desired to prepare The compounds of formula (I) wherein $R^1$ and $R^2$ form together methylidene may be prepared starting from (2-methylcyclopent-1-en-1-yl)methanol (7) via a Johnson-Claisen rearrangement. Cyclopropanation or hydrogenation of the exo-methylene group of compounds 8 by methods known in the art may lead to the desired esters 4 (wherein X=CO$_2$Et and either $R^1$ or $R^2$=H) and 9.

Scheme 1:

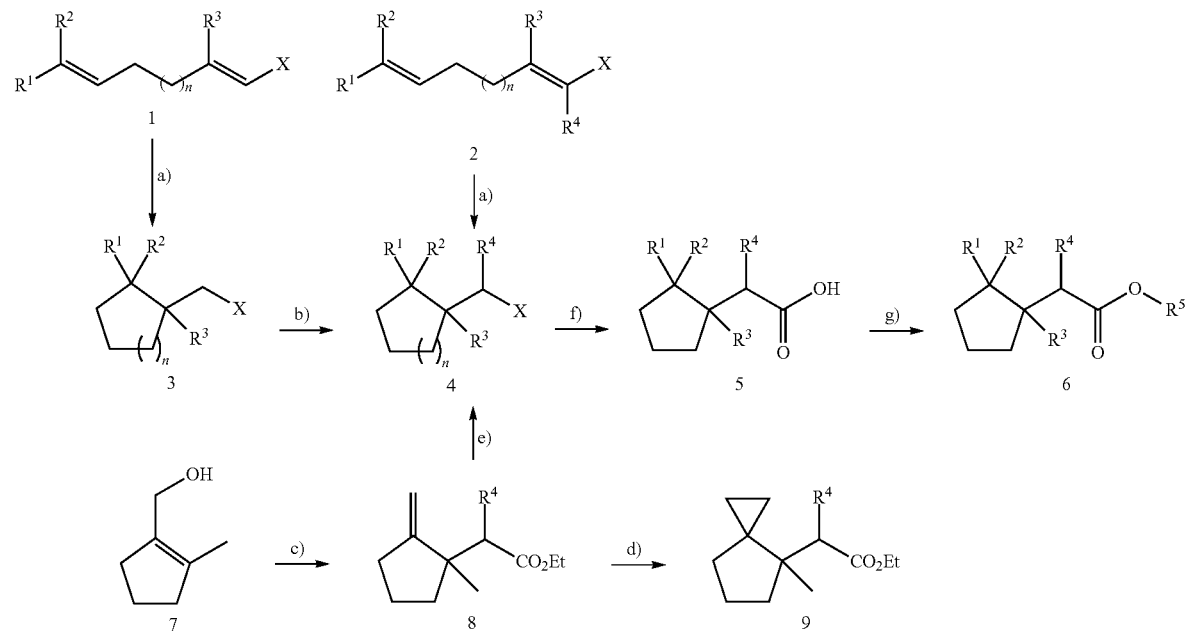

a) Fe(acac)$_3$, PhSiH$_3$ or PMHS, EtOH/ethylene glycol;
b) LDA, $R^4$I or $R^4$Br, THF;
c) 1,1,1-triethoxyethane or 1,1,1-triethoxy-propane, propionic acid, 160° C;
d) CH$_2$ICl, Et$_2$Zn, DCE;
e) if X = CO$_2$Et: H$_2$, Pd/C, EtOH;
f) if X = CO$_2$Et: NaOH, MeOH/H$_2$O;
g) $R^5$OH, H$_2$SO$_4$, reflux; $R^1$ - $R^5$ and X have the same meaning as given for formula (I), n = 1, 2.

individual stereoisomers, this may be achieved according to methodology known in the art, e.g. by preparative HPLC and GC or by stereoselective synthesis.

Most of the compounds as herein above described are accessible by applying the methodology published by P. Baran et al. (*J. Am. Chem. Soc.* 2014, 136, 1304). In particular, the compounds of formula (I), with the exception of compounds of formula (I) wherein $R^1$ and $R^2$ form together methylidene, may be prepared in 1-4 steps according to Scheme 1, starting from the corresponding 1,5- or 1,6-dienes 1 or 2. The latter may be converted into the corresponding cyclopentyl or cyclohexyl derivatives 3 or 4 via a reductive olefin coupling preferably using a catalytic amount of an Fe(III) or a Co(III) salt (e.g. Fe(acac)$_3$, Co(acac)$_3$, Fe$_2$(ox)$_3$.6H$_2$O, Fe(dibm)$_3$), a reductant (e.g. PhSiH$_3$, PMHS, NaBH$_4$) and a protic solvent (e.g. EtOH, ethylene glycol). The 1,5- or 1,6-dienes 1 or 2 used for the reductive olefin coupling are either commercially available or may be prepared for example via a Wittig-Horner reaction from the corresponding aldehydes or ketones. Saponification of the ester of compounds 4 (wherein X=CO$_2$Et) leads to carboxylic acids 5 which can be converted into compounds 6 via acid or base catalyzed esterification.

The invention is now further described with reference to the following non-limiting examples. These examples are for the purpose of illustration only and it is understood that variations and modifications can be made by one skilled in the art.

All products were purified after work-up by either flash chromatography (FC) using Merck silica gel 60 (particle size 0.040-0.063 mm) or distillation. NMR spectra were measured in CDCl$_3$ or C$_6$D$_6$ and are reported relative to TMS ($^1$H NMR spectrum) or relative to CDCl$_3$ ($^{13}$C NMR spectrum) as follows: chemical shifts (δ ppm), coupling constants J in Hz. GC-MS analyses were run on a MSD5975C mass spectrometer and are reported as m/z list (relative intensity). Odor description refers to the odor of the isomeric mixture of the compounds unless otherwise indicated.

EXAMPLE 1: SYNTHESIS OF ETHYL 2-(1,2,2-TRIMETHYLCYCLOPENTYL)PROPANOATE a) Synthesis of ethyl 2,3,7-trimethylocta-2,6-dienoate Ethyl 2-(diethoxyphosphoryl)propanoate (1133 g, 4.76 mol) was added to a suspension of potassium t-butylat (450 g, 4.04 mol) in toluene (2.8 l) at 25-35° C. After the yellow suspension was stirred at 25° C. for 30 min, 6-methylhept-5-en-2-one (300 g, 2.38 mol) in toluene (0.2 L) was added at 5-15° C., and the mixture was stirred at 25° C. for 20 h. After addition of 2M aq. HCl-solution, the phases were separated and the aq. layer was extracted with hexane. The org. phases were washed with $H_2O$ and brine, dried ($MgSO_4$), filtered and the filtrate was concentrated. The residue was re-dissolved in hexane and the org. phase was washed with 2M aq. HCl (2×), 15% aq. $Na_2CO_3$ and brine, dried ($MgSO_4$), filtered and the filtrate was concentrated. The crude product was purified by distillation (b.p. 75° C., 0.13 mbar) to yield 410 g (82%) of ethyl 2,3,7-trimethyl-octa-2,6-dienoate (mixture of E/Z-isomers; ratio 1.2:1) as a colorless oil.

$^1$H NMR ($CDCl_3$, 400 MHz); mixture of E/Z-isomers: δ=5.16-5.10 (m, 2H), 4.19 (q, J=7.2 Hz, 2H), 4.18 (q, J=7.2 Hz, 2H), 2.37-2.33 (m, 2H), 2.17-2.07 (m, 6H), 1.99 (q, J=1.5 Hz, 3H), 1.87 (q, J=1.5 Hz, 3H), 1.84 (q, J=1.0 Hz, 3H), 1.79 (q, J=1.0 Hz, 3H), 1.69 (br. q, J=1.0 Hz, 3H), 1.68 (br. q, J=1.2 Hz, 3H), 1.61 (br. s, 6H), 1.30 (t, J=7.1 Hz, 3H), 1.29 (t, J=7.1 Hz, 3H) ppm.

$^{13}$C-NMR ($CDCl_3$, 100 MHz); mixture of E/Z-isomers: δ=169.9 (s), 169.7 (s), 145.9 (s), 145.5 (s), 132.2 (s), 131.7 (s), 123.9 (d), 123.5 (d), 123.0 (s), 122.8 (s), 59.9 (2t), 36.4 (t), 36.1 (t), 27.1 (t), 25.9 (t), 25.6 (2q), 20.9 (q), 20.2 (q), 17.5 (q), 17.5 (q), 15.8 (q), 15.2 (q), 14.2 (q), 14.2 (q) ppm.

MS (EI, tR=7.12 min); major isomer: 210 (1, [M]$^{+\cdot}$), 165 (13, [M]$^{+\cdot}$-EtO$^{\cdot}$), 142 (18), 137 (18), 96 (36), 69 (100), 67 (15), 53 (13), 43 (10), 41 (58), 39 (9), 29 (8).

MS (EI, tR=6.92 min); minor isomer: 210 (2, [M]$^{+\cdot}$), 165 (10, [M]$^{+\cdot}$-EtO$^{\cdot}$), 142 (25), 137 (27), 97 (12), 96 (53), 69 (100), 67 (21), 53 (17), 43 (16), 41 (71), 39 (12), 29 (10).

b) Synthesis of ethyl 2-(1,2,2-trimethylcyclopentyl)propanoate

Polymethylhydrosiloxane (25 g) was added to a suspension of ethyl 2,3,7-trimethylocta-2,6-dienoate (52.6 g, 250 mmol) and Fe(acac)$_3$ (26.5 g, 75 mmol) in ethanol/ethylene glycol (450 ml; ratio 5:1) at 25° C. The mixture was stirred at 60° C. for 3 h, cooled to 25° C., filtered through a pad of Celite and washed with hexane. After addition of $H_2O$, the phases were separated and the aq. layer was extracted with hexane. The org. phases were washed with $H_2O$, dried ($MgSO_4$), filtered and the filtrate was concentrated. The residue was filtered through a pad of $SiO_2$ and washed with hexane/EtOAc (19:1). The filtrate was concentrated to yield 51.6 g (94%, purity 97%) of ethyl 2-(1,2,2-trimethylcyclopentyl)propanoate as a mixture of two diastereomers (ratio 2.2:1) as a colorless oil. An olfactive pure sample was obtained by distillation or purification by flash chromatography on $SiO_2$ (hexane/EtOAc 99:1→98:2).

$^1$H NMR ($CDCl_3$, 400 MHz); mixture of two diastereomers: δ=4.15-4.03 (m, 4H), 2.62 (q, J=7.1 Hz, 1H), 2.55 (q, J=7.1 Hz, 1H), 1.93-1.84 (m, 1H), 1.79-1.50 (m, 8H), 1.44-1.32 (m, 3H), 1.27 (t, J=7.1 Hz, 3H), 1.25 (t, J=7.1 Hz, 3H), 1.14 (d, J=7.1 Hz, 3H), 1.12 (d, J=7.1 Hz, 3H), 1.02 (s, 3H), 1.01 (s, 3H), 1.00 (s, 3H), 0.96 (d, J=0.7 Hz, 3H), 0.95 (s, 3H), 0.81 (s, 3H) ppm.

$^{13}$C-NMR ($CDCl_3$, 100 MHz); mixture of two diastereomers: δ=176.3 (s), 176.2 (s), 59.7 (t), 59.7 (t), 48.2 (s), 46.6 (s), 45.2 (d), 44.4 (s), 44.3 (d), 43.9 (s), 41.4 (t), 41.4 (t), 38.7 (t), 38.6 (t), 25.3 (q), 25.2 (q), 24.6 (q), 23.1 (q), 19.2 (t), 18.4 (t), 16.8 (q), 16.7 (q), 15.1 (q), 14.3 (q), 14.1 (q), 13.2 (q) ppm.

MS (EI, tR=6.88 min); major isomer: 212 (1, [M]$^{+\cdot}$), 197 (4), 166 (35, [M]$^{+\cdot}$-EtOH), 141 (10), 139 (11), 127 (13), 111 (26), 109 (19), 102 (100), 95 (30), 83 (35), 69 (64), 57 (21), 55 (50), 43 (12), 41 (37), 29 (19).

MS (EI, tR=6.79 min); minor isomer: 212 (1, [M]$^{+\cdot}$), 197 (5), 169 (27), 166 (44, [M]$^{+\cdot}$ EtOH), 141 (19), 139 (12), 127 (13), 124 (13), 123 (12), 111 (26), 109 (22), 102 (100), 95 (38), 83 (35), 69 (69), 57 (23), 55 (57), 43 (15), 41 (44), 29 (23).

Odor description: fruity agrestic, strawberry, apple, sparkling with a champagne feeling, slightly floral rosy.

EXAMPLE 2: SYNTHESIS OF METHYL 2-(1,2,2-TRIMETHYLCYCLOPENTYL)PROPANOATE a) Synthesis of methyl 2-(1,2,2-trimethylcyclopentyl)acetate Phenylsilane (4.6 ml, 37.5 mmol) was added to a suspension of methyl 3,7-dimethylocta-2,6-dienoate (4.9 ml, 25.0 mmol) and Fe(acac)$_3$ (2.65 g, 7.50 mmol) in ethanol/ethylene glycol (90 ml; ratio 5:1) at 25° C. The mixture was stirred at 60° C. for 1 h, cooled to 25° C., filtered through a pad of Celite and washed with hexane. After addition of $H_2O$, the phases were separated and the aq. layer was extracted with hexane. The org. phases were washed with brine, dried ($MgSO_4$), filtered and the filtrate was concentrated. The residue was purified by flash chromatography on $SiO_2$ (hexane/EtOAc 98:2→95:5) to yield 4.06 g (80%, purity 91%) of methyl 2-(1,2,2-trimethylcyclopentyl)acetate as a colorless oil.

$^1$H NMR ($CDCl_3$, 400 MHz): δ=3.65 (s, 3H), 2.27-2.19 (m, 2H), 1.89-1.80 (m, 1H), 1.66-1.57 (m, 4H), 1.51-1.45 (m, 1H), 0.93 (s, 3H), 0.88 (s, 3H), 0.85 (s, 3H) ppm.

$^{13}$C-NMR ($CDCl_3$, 100 MHz): δ=173.9 (s), 51.1 (q), 45.2 (s), 43.9 (s), 41.4 (t), 39.0 (t), 36.8 (t), 24.5 (q), 23.6 (q), 21.1 (q), 19.4 (t) ppm.

MS (EI): 184 (1, [M]$^{+\cdot}$), 169 (7), 153 (31), 152 (100, [M]$^{+\cdot}$-MeOH), 141 (32), 111 (58), 110 (95), 109 (42), 96 (30), 95 (89), 94 (35), 82 (32), 69 (65), 59 (23), 55 (67), 41 (66), 29 (19).

Odor description: green fruity woody.

b) Synthesis of methyl 2-(1,2,2-trimethylcyclopentyl)propanoate

Methyl 2-(1,2,2-trimethylcyclopentyl)acetate (1.13 g, 6.13 mmol) in THF (3 ml) was added to a solution of LDA (freshly prepared from BuLi (3.8 ml, 6.13 mmol) and diisopropylamine (0.9 ml, 6.13 mmol)) in THF (6 ml) at −78° C. The mixture was stirred at −78° C. for 1 h before MeI (0.4 ml, 6.75 mmol) in THF (3 ml) was added at −78° C. The mixture was stirred at −78° C. for 1.5 h and at 25° C. for 2 h. After addition of sat. aq. $NH_4Cl$-solution, the phases were separated and the aq. layer was extracted with MTBE. The org. phases were dried ($MgSO_4$), filtered and the filtrate was concentrated. The residue was purified by flash chromatography on $SiO_2$ (hexane/EtOAc 98:2) to yield 0.67 g (51%, purity 93%) of methyl 2-(1,2,2-trimethylcyclopentyl)propanoate as a mixture of two diastereomers (ratio 2.5:1) as a light yellow oil.

$^1$H NMR ($CDCl_3$, 400 MHz); mixture of two diastereomers: δ=3.65 (s, 3H), 3.63 (s, 3H), 2.65 (q, J=7.1 Hz, 1H), 2.58 (q, J=7.1 Hz, 1H), 1.89-1.30 (m, 12H), 1.14 (d, J=7.1 Hz, 3H), 1.12 (d, J=7.1 Hz, 3H), 1.01 (br. s, 6H), 0.99 (s, 3H), 0.96 (d, J=1.0 Hz, 3H), 0.95 (s, 3H), 0.79 (s, 3H) ppm.

¹³C-NMR (CDCl₃, 100 MHz); mixture of two diastereomers: δ=176.8 (s), 176.7 (s), 51.0 (q), 50.9 (q), 48.2 (s), 46.6 (s), 45.1 (d), 44.4 (s), 44.1 (d), 43.9 (s), 41.4 (t), 41.3 (t), 38.7 (t), 38.6 (t), 25.3 (q), 25.2 (q), 24.6 (q), 23.0 (q), 19.2 (t), 18.4 (t), 16.8 (q), 16.6 (q), 15.1 (q), 13.2 (q) ppm.

MS (EI, tR=6.29 min); major isomer: 198 (1, [M]⁺·), 183 (4), 166 (37, [M]⁺·-MeOH), 155 (39), 139 (6), 111 (42), 95 (50), 88 (100), 83 (40), 69 (87), 67 (27), 59 (27), 55 (90), 41 (75), 29 (18).

MS (EI, tR=6.38 min); minor isomer: 198 (1, [M]⁺·), 183 (4), 166 (32, [M]⁺·-MeOH), 139 (6), 127 (13), 111 (42), 102 (53), 95 (40), 88 (100), 83 (42), 69 (84), 59 (26), 57 (33), 55 (86), 43 (11), 41 (75), 29 (18).

Odor description: fruity agrestic, strawberry, raspberry, bornyl fruity minty.

EXAMPLE 3 a) Synthesis of 2-(1,2,2-trimethylcyclopentyl)propanoic acid

Sodium hydroxide (11.0 g, 274 mmol) was added to ethyl 2-(1,2,2-trimethylcyclopentyl)-propanoate (Example 1) (4.17 g, 19.6 mmol) in MeOH (30 ml) and H₂O (10 ml) at 25° C. and the reaction mixture was stirred at reflux for 20 h. After addition of 2M aq. NaOH-solution, the aq. layer was extracted with MTBE (2×). The aq. phase was acidified with conc. HCl until a pH of 1 was reached and extracted again with MTBE (2×). The org. phases were dried (MgSO₄), filtered and the filtrate was concentrated to yield 3.13 g (86%) of 2-(1,2,2-trimethylcyclopentyl)propanoic acid as a white solid.

b) Synthesis of propyl 2-(1,2,2-trimethylcyclopentyl)propanoate

Sulfuric acid (0.5 ml, 9.23 mmol) was added to 2-(1,2,2-trimethylcyclopentyl)propanoic acid (1.70 g, 9.23 mmol) in propan-1-ol (20.8 ml, 276 mmol) at 25° C. and the reaction mixture was stirred at reflux for 24 h. After addition of H₂O, the aq. layer was extracted with MTBE (2×). The org. phases were washed with 50% aq. NaOH-solution (3×) and brine, dried (MgSO₄), filtered and the filtrate was concentrated. The residue was purified by flash chromatography on SiO₂ (hexane/EtOAc 95:5) to yield 0.87 g (39%, purity 94%) of propyl 2-(1,2,2-trimethylcyclopentyl)propanoate as a mixture of two diastereomers (ratio 22:1) as a colorless oil.

¹³C-NMR (CDCl₃, 100 MHz); major isomer: δ=176.4 (s), 65.5 (t), 46.5 (s), 45.3 (d), 44.4 (s), 41.4 (t), 38.8 (t), 25.3 (2q), 22.0 (t), 19.2 (t), 16.9 (q), 13.3 (q), 10.6 (q) ppm.

MS (EI); major isomer: 226 (1, [M]⁺·), 211 (2), 167 (18), 166 (41), 139 (17), 116 (78), 111 (36), 109 (30), 95 (41), 83 (49), 74 (53), 69 (100), 57 (50), 55 (92), 43 (63), 41 (85), 29 (13), 27 (15).

Odor description: fruity sweet agrestic, slightly woody.

c) Synthesis of isopropyl 2-(1,2,2-trimethylcyclopentyl)propanoate

According to Example 3b, starting from 2-(1,2,2-trimethylcyclopentyl)propanoic acid (1.34 g, 7.27 mmol) and propan-2-ol (16.7 ml, 218 mmol), 0.80 g (46%, purity 94%) of isopropyl 2-(1,2,2-trimethylcyclopentyl)propanoate was obtained after purification by FC on SiO₂ (hexane/EtOAc 95:5) as a mixture of two diastereomers (ratio 6:1) as a colorless oil.

¹³C-NMR (CDCl₃, 100 MHz); major isomer: δ=175.8 (s), 66.9 (d), 46.6 (s), 45.4 (d), 44.5 (s), 41.4 (t), 38.7 (t), 25.3 (q), 25.2 (q), 21.9 (q), 21.8 (q), 19.2 (t), 16.9 (q), 13.2 (q) ppm.

MS (EI); major isomer: 226 (1, [M]⁺·), 211 (1), 184 (5), 183 (6), 166 (42), 139 (16), 116 (37), 111 (64), 109 (37), 95 (36), 83 (43), 74 (41), 69 (100), 57 (52), 55 (77), 43 (67), 41 (64), 29 (8), 27 (8).

Odor description: fruity raspberry.

d) Synthesis of but-3-en-1-yl 2-(1,2,2-trimethylcyclopentyl)propanoate

According to Example 3b, starting from 2-(1,2,2-trimethylcyclopentyl)propanoic acid (1.00 g, 5.43 mmol) and but-3-en-1-ol (7.0 ml, 81 mmol), 0.27 g (20%, purity 96%) of but-3-en-1-yl 2-(1,2,2-trimethylcyclopentyl)propanoate was obtained after purification by FC on SiO₂ (hexane/EtOAc 98:2) as a mixture of two diastereomers (ratio>30:1) as a colorless oil.

¹³C-NMR (CDCl₃, 100 MHz); major isomer: δ=176.3 (s), 134.2 (d), 117.1 (t), 63.0 (t), 46.5 (s), 45.3 (d), 44.5 (s), 41.4 (t), 38.8 (t), 33.1 (t), 25.3 (q), 25.3 (q), 19.2 (t), 16.9 (q), 13.3 (q) ppm.

MS (EI); major isomer: 238 (1, [M]⁺·), 223 (1), 167 (8), 166 (18), 139 (6), 124 (5), 111 (12), 109 (19), 95 (16), 86 (30), 83 (16), 69 (41), 57 (20), 55 (100), 41 (27), 29 (8).

Odor description: fruity apple.

e) Synthesis of isobutyl 2-(1,2,2-trimethylcyclopentyl)propanoate

According to Example 3b, starting from 2-(1,2,2-trimethylcyclopentyl)propanoic acid (0.76 g, 4.12 mmol) and 2-methylpropan-1-ol (11.5 ml, 124 mmol), 0.82 g (77%, purity 93%) of isobutyl 2-(1,2,2-trimethylcyclopentyl)propanoate was obtained after purification by distillation (Kugelrohr apparatus, 90° C., 0.10 torr) as a mixture of two diastereomers (ratio 10:1) as a colorless oil.

¹³C-NMR (CDCl₃, 100 MHz); major isomer: δ=176.4 (s), 70.2 (t), 46.5 (s), 45.5 (d), 44.5 (s), 41.4 (t), 38.8 (t), 27.7 (d), 25.3 (q), 25.3 (q), 19.3 (q), 19.3 (q), 19.2 (t), 16.9 (q), 13.3 (q) ppm MS (EI); major isomer: 240 (1, [M]⁺·), 225 (1), 184 (2), 167 (16), 166 (29, [M]⁺·-iBuOH), 139 (14), 130 (20), 124 (8), 111 (39), 109 (23), 95 (23), 83 (28), 74 (26), 69 (63), 57 (100), 55 (61), 41 (58), 29 (15).

Odor description: fruity acidic, slightly agrestic.

f) Synthesis of allyl 2-(1,2,2-trimethylcyclopentyl)propanoate

According to Example 3b, starting from 2-(1,2,2-trimethylcyclopentyl)propanoic acid (3.31 g, 18.0 mmol) and prop-2-en-1-ol (18.3 ml, 269 mmol), 1.91 g (44%, purity 93%) of allyl 2-(1,2,2-trimethylcyclopentyl)propanoate was obtained after purification by FC on SiO₂ (hexane/EtOAc 98:2→95:5) as a mixture of two diastereomers (ratio 18:1) as a colorless oil.

¹³C-NMR (CDCl₃, 100 MHz); major isomer: δ=175.9 (s), 132.5 (d), 118.1 (t), 64.6 (t), 46.6 (s), 45.2 (d), 44.5 (s), 41.4 (t), 38.7 (t), 25.2 (q), 25.2 (q), 19.2 (t), 16.8 (q), 13.2 (q) ppm.

MS (EI); major isomer: 224 (1, [M]⁺·), 209 (2), 183 (5), 166 (24), 127 (11), 114 (17), 111 (15), 109 (49), 95 (22), 83 (20), 81 (16), 69 (100), 57 (35), 55 (61), 41 (75), 29 (7).

Odor description: fruity acidic, chemical agrestic.

EXAMPLE 4 a) Synthesis of methyl 2-(1-methylspiro[4.4]nonan-1-yl)acetate

According to Example 1 b, starting from methyl 6-cyclopentylidene-3-methylhex-2-enoate (prepared from cyclopentanone by methods known to the person skilled in the art) (4.17 g, 13.0 mmol), 1.23 g (44%, purity 98%) of methyl 2-(1-methylspiro[4.4]nonan-1-yl)acetate was obtained after purification by FC on $SiO_2$ (hexane/EtOAc 95:5) as a colorless oil.

$^1$H NMR ($CDCl_3$, 400 MHz): δ=3.65 (s, 3H), 2.29 (d, J=13.0 Hz, 1H), 2.20 (d, J=13.0 Hz, 1H), 1.79-1.73 (m, 1H), 1.68-1.53 (m, 9H), 1.51-1.38 (m, 2H), 1.30-1.19 (m, 2H), 0.96 (s, 3H) ppm.

$^{13}$C-NMR ($CDCl_3$, 100 MHz): δ=173.8 (s), 56.6 (s), 51.1 (q), 45.0 (s), 41.4 (t), 37.3 (t), 36.8 (t), 33.0 (t), 32.8 (t), 24.2 (t), 24.0 (t), 20.9 (q), 19.6 (t) ppm.

MS (EI): 195 (1, [M]$^{+\cdot}$—$CH_3$), 178 (49, [M]$^{+\cdot}$-MeOH), 167 (13), 137 (42), 136 (69), 129 (29), 121 (24), 108 (27), 96 (51), 95 (73), 94 (49), 93 (44), 82 (39), 81 (77), 74 (15), 67 (100), 59 (20), 55 (46), 41 (50), 29 (10).

Odor description: fruity peppery, woody green, pine needle resinous terpenic.

b) Synthesis of methyl 2-(1-methylspiro[4.4]nonan-1-yl)propanoate

According to Example 2b, starting from methyl 2-(1-methylspiro[4.4]nonan-1-yl)acetate (0.91 g, 4.33 mmol), 0.54 g (53%, purity 95%) of methyl 2-(1-methylspiro[4.4]nonan-1-yl)propanoate was obtained after purification by FC on $SiO_2$ (hexane/EtOAc 99:1) as a mixture of two diastereomers (ratio 2.2:1) as a colorless oil.

$^1$H NMR ($CDCl_3$, 400 MHz); mixture of two diastereomers: δ=3.63 (s, 3H), 3.62 (s, 3H), 2.67 (q, J=7.1 Hz, 1H), 2.64 (q, J=7.1 Hz, 1H), 1.84-1.18 (m, 28H), 1.14 (d, J=7.0 Hz, 3H), 1.13 (d, J=7.1 Hz, 3H), 1.00 (s, 3H), 1.00 (s, 3H) ppm.

$^{13}$C-NMR ($CDCl_3$, 100 MHz); mixture of two diastereomers: δ=176.9 (s), 176.8 (s), 57.1 (s), 56.7 (s), 51.0 (q), 50.8 (q), 48.0 (s), 46.0 (s), 45.3 (d), 43.9 (d), 39.5 (t), 39.0 (t), 38.9 (t), 38.8 (t), 34.7 (t), 33.3 (t), 33.0 (t), 31.5 (t), 24.2 (t), 24.0 (t), 23.8 (t), 23.6 (t), 19.6 (t), 18.7 (t), 17.3 (q), 17.2 (q), 15.1 (q), 13.1 (q) ppm.

MS (EI, tR=7.91 min); major isomer: 224 (2, [M]$^{+\cdot}$), 209 (4), 192 (43, [M]$^{+\cdot}$-MeOH), 181 (64), 137 (78), 136 (29), 121 (19), 115 (29), 110 (33), 109 (34), 95 (77), 93 (29), 88 (100), 83 (25), 81 (67), 79 (33), 69 (21), 67 (60), 59 (22), 55 (38), 41 (45), 29 (11).

MS (EI, tR=8.10 min); minor isomer: 224 (2, [M]$^{+\cdot}$), 209 (3), 192 (38, [M]$^{+\cdot}$-MeOH), 165 (13), 137 (73), 136 (30), 110 (41), 109 (36), 95 (75), 93 (27), 88 (100), 83 (26), 81 (69), 79 (30), 67 (58), 59 (22), 55 (33), 41 (41), 29 (10).

Odor description: fruity, woody ambery, myraldyl effect.

c) Synthesis of ethyl 2-(1-methylspiro[4.4]nonan-1-yl)acetate

According to Example 1 b, starting from ethyl 6-cyclopentylidene-3-methylhex-2-enoate (prepared from cyclopentanone by methods known to the person skilled in the art) (6.29 g, 28.3 mmol), 5.77 g (88%, purity 96%) of ethyl 2-(1-methylspiro[4.4]nonan-1-yl)acetate was obtained after purification by distillation (Kugelrohr apparatus, 140° C., 0.06 torr) as a colorless oil.

$^1$H NMR ($CDCl_3$, 400 MHz): δ=4.12 (q, J=7.1 Hz, 1H), 4.11 (q, J=7.1 Hz, 1H), 2.27 (d, J=13.0 Hz, 1H), 2.18 (d, J=13.0 Hz, 1H), 1.81-1.70 (m, 1H), 1.65-1.54 (m, 9H), 1.54-1.39 (m, 2H), 1.30-1.19 (m, 2H), 1.26 (t, J=7.1 Hz, 3H), 0.97 (s, 3H) ppm.

$^{13}$C-NMR ($CDCl_3$, 100 MHz): δ=173.4 (s), 59.9 (t), 56.6 (s), 45.0 (s), 41.6 (t), 37.3 (t), 36.8 (t), 33.0 (t), 32.8 (t), 24.2 (t), 24.0 (t), 20.9 (q), 19.6 (t), 14.3 (q) ppm.

MS (EI): 224 (1, [M]$^{+\cdot}$), 209 (1), 195 (1), 178 (55, [M]$^{+\cdot}$-EtOH), 143 (22), 137 (62), 136 (66), 121 (23), 115 (21), 108 (28), 107 (26), 96 (56), 95 (82), 94 (50), 93 (44), 88 (19), 81 (92), 79 (46), 67 (100), 55 (55), 41 (61), 29 (42).

Odor description: fruity, woody ambery, myraldyl effect.

d) Synthesis of ethyl 2-(1-methylspiro[4.4]nonan-1-yl)propanoate

According to Example 1 b, starting from ethyl 6-cyclopentylidene-2,3-dimethylhex-2-enoate (prepared from 5-cyclopentylidenepentan-2-one by methods known to the person skilled in the art) (4.51 g, 19.1 mmol), 4.19 g (90%, purity 98%) of ethyl 2-(1-methylspiro[4.4]nonan-1-yl)propanoate was obtained after purification by FC on $SiO_2$ (hexane/EtOAc 99:1) as a mixture of two diastereomers (ratio 1.6:1) as a colorless oil.

$^1$H NMR ($CDCl_3$, 400 MHz); mixture of two diastereomers: δ=4.15-4.03 (m, 4H), 2.64 (q, J=7.1 Hz, 1H), 2.61 (q, J=7.0 Hz, 1H), 1.87-1.21 (m, 28H), 1.25 (t, J=7.1 Hz, 3H), 1.25 (t, J=7.1 Hz, 3H), 1.14 (d, J=7.0 Hz, 3H), 1.13 (d, J=7.1 Hz, 3H), 1.01 (d, J=0.6 Hz, 3H), 1.00 (d, J=0.4 Hz, 3H) ppm.

$^{13}$C-NMR ($CDCl_3$, 100 MHz); mixture of two diastereomers: 0.3=176.4 (s), 176.3 (s), 59.7 (t), 59.6 (t), 57.1 (s), 56.8 (s), 47.9 (s), 46.0 (s), 45.4 (d), 44.2 (d), 39.5 (t), 39.0 (t), 39.0 (t), 38.5 (t), 34.7 (t), 33.4 (t), 33.0 (t), 31.4 (t), 24.2 (t), 23.8 (t), 23.6 (t), 23.6 (t), 19.6 (t), 18.8 (t), 17.3 (q), 17.2 (q), 15.1 (q), 14.3 (q), 14.1 (q), 13.1 (q) ppm.

MS (EI, tR=8.49 min); major isomer: 238 (2, [M]$^{+\cdot}$), 223 (3), 192 (29, [M]$^{+\cdot}$-EtOH), 165 (14), 137 (41), 129 (16), 111 (18), 110 (28), 109 (25), 102 (100), 95 (50), 83 (18), 81 (43), 79 (20), 69 (16), 67 (36), 55 (24), 41 (27), 29 (24).

MS (EI, tR=8.28 min); minor isomer: 238 (2, [M]$^{+\cdot}$), 223 (3), 195 (37), 192 (34, [M]$^{+\cdot}$ EtOH), 165 (11), 137 (46), 129 (19), 111 (18), 110 (24), 109 (24), 102 (100), 95 (49), 93 (20), 83 (18), 81 (44), 79 (22), 69 (18), 67 (37), 55 (27), 41 (30), 29 (27).

Odor description: woody ambery, fruity winey, pear.

EXAMPLE 5 a) Synthesis of ethyl 2-(1-methyl-2-methylenecyclopentyl)propanoate

A solution of (2-methylcyclopent-1-en-1-yl)methanol (3.33 g, 29.7 mmol), 1,1,1-triethoxypropane (17.7 ml, 89.1 mmol) and propionic acid (0.22 ml, 2.97 mmol) was stirred at 90° C. for 2 h and at 160° C. for 2 h while the volatiles were distilled off. After cooling to 25° C. and addition of $H_2O$, the aq. layer was extracted with MTBE (2×). The org. phases were washed with brine, dried ($MgSO_4$), filtered and the filtrate was concentrated. The volatiles were further removed by distillation (Kugelrohr apparatus, 40° C., 0.07 torr) and the residue was purified by flash chromatography on $SiO_2$ (hexane/EtOAc 199:1→99:1→98:2) to yield 3.25 g (53%, purity 95%) of ethyl 2-(1-methyl-2-methylenecyclopentyl)propanoate as a mixture of two diastereomers (ratio 5.5:1) as a colorless oil.

$^1$H NMR (CDCl$_3$, 400 MHz); mixture of two diastereomers: δ=4.93 (t, J=2.1 Hz, 1H), 4.90 (t, J=2.0 Hz, 1H), 4.77 (t, J=2.2 Hz, 1H), 4.70 (t, J=2.2 Hz, 1H), 4.12 (q, J=7.1 Hz, 2H), 4.08 (q, J=7.1 Hz, 2H), 2.59 (q, J=6.9 Hz, 1H), 2.55 (q, J=7.1 Hz, 1H), 2.47-2.26 (m, 4H), 2.14 (ddd, J=12.5, 8.1, 7.3 Hz, 1H), 2.00 (ddd, J=13.0, 9.0, 7.1 Hz, 1H), 1.77-1.53 (m, 4H), 1.48-1.39 (m, 2H), 1.27 (t, J=7.1 Hz, 3H), 1.24 (t, J=7.1 Hz, 3H), 1.16 (d, J=7.3 Hz, 3H), 1.10 (s, 3H), 1.09 (d, J=6.9 Hz, 3H), 1.08 (s, 3H) ppm.

$^{13}$C-NMR (CDCl$_3$, 100 MHz); mixture of two diastereomers: δ=175.8 (s), 175.7 (s), 159.3 (s), 159.1 (s), 105.2 (t), 104.4 (t), 59.8 (t), 59.7 (t), 47.6 (d), 47.0 (s), 46.9 (s), 46.0 (d), 36.7 (t), 35.5 (t), 34.5 (t), 33.6 (t), 26.7 (q), 24.7 (q), 22.8 (t), 22.0 (t), 14.3 (q), 14.2 (q), 13.2 (q), 13.1 (q) ppm MS (EI, tR=6.04 min); major isomer: 196 (<1, [M]$^{+\cdot}$), 181 (<1, [M]$^{+\cdot}$—CH$_3$), 151 (1, [M]$^{+\cdot}$-Eta), 123 (3), 109 (9), 102 (10), 96 (8), 95 (100), 93 (9), 79 (10), 74 (6), 67 (12), 55 (7), 53 (5), 45 (1), 41 (8), 29 (12).

MS (EI, tR=5.95 min); minor isomer: 196 (<1, [M]$^{+\cdot}$), 181 (<1, [M]$^{+\cdot}$—CH$_3$), 151 (1, [M]$^{+\cdot}$-EtO$^\cdot$), 123 (1), 109 (10), 102 (11), 96 (8), 95 (100), 93 (7), 79 (10), 74 (6), 67 (10), 55 (6), 53 (4), 45 (1), 41 (7), 29 (11).

Odor description: fruity banana, slightly agrestic, fruity red fruits strawberry apple.

b) Synthesis of ethyl 2-(4-methylspiro[2.4]heptan-4-yl)propanoate

Chloroiodomethane (1.8 ml, 24.5 mmol) was added to a solution of ethyl 2-(1-methyl-2-methylenecyclopentyl)propanoate (1.50 g, 7.64 mmol) in 1,2-dichloroethane (25 ml) at 0° C. After the reaction mixture was stirred at 0° C. for 10 min, diethylzinc (1.5 M in toluene, 8.2 ml, 12.2 mmol) was added at 0° C., and the suspension was stirred at 25° C. for 3 h. The reaction mixture was cooled to 0° C. and again chloroiodomethane (1.8 ml, 24.5 mmol) followed by diethylzinc (1.5M in toluene, 8.2 ml, 12.2 mmol) were added. After further stirring of the suspension for 3 h, 1 M aq. HCl-solution was added, and the aq. layer was extracted with CH$_2$Cl$_2$ (3×). The org. phases were dried (MgSO$_4$), filtered and the filtrate was concentrated. The crude product was purified by flash chromatography on SiO$_2$ (cyclohexane/EtOAc 99:1→98:2) to yield 0.91 g (47%, purity 83%) of ethyl 2-(4-methylspiro[2.4]heptan-4-yl)propanoate as a single isomer as a light yellow oil. An olfactive pure and colorless sample was obtained by further distillations.

$^1$H NMR (CDCl$_3$, 400 MHz): δ=4.14-4.02 (m, 2H), 2.27 (q, J=6.9 Hz, 1H), 2.02 (ddd, J=13.0, 7.8, 6.9 Hz, 1H), 1.90 (dt, J=12.5, 8.6 Hz, 1H), 1.74-1.58 (m, 2H), 1.45 (ddd, J=13.0, 8.6, 6.0 Hz, 1H), 1.36 (ddd, J=12.5, 8.1, 4.3 Hz, 1H), 1.25 (t, J=7.1 Hz, 3H), 1.15 (d, J=6.9 Hz, 3H), 0.81 (s, 3H), 0.51-0.40 (m, 3H), 0.17-0.13 (m, 1H) ppm.

$^{13}$C-NMR (CDCl$_3$, 100 MHz): δ=176.2 (s), 59.7 (t), 45.0 (d), 43.5 (s), 37.6 (t), 37.2 (2t), 29.9 (s), 22.0 (t), 21.3 (q), 14.2 (q), 13.6 (q), 11.1 (t), 8.6 (t) ppm.

MS (EI): 210 (1, [M]$^{+\cdot}$), 195 (1), 182 (8), 165 (5, [M]$^{+\cdot}$-Eta), 109 (100), 108 (39), 102 (26), 93 (18), 81 (18), 79 (17), 74 (13), 67 (21), 55 (11), 41 (12), 29 (19).

Odor description: fruity banana, fruity rosy apple green, reminiscent of isocyclocitral and α-damascone.

EXAMPLE 6 a) Synthesis of ethyl 3,7-dimethylnona-2,6-dienoate

Pd(Pb)/CaCO$_3$ (Lindlar catalyst, 0.8 g) was added to a solution of 3-methylpent-1-yn-3-ol (16.4 g, 167 mmol) in hexane (250 ml) at 25° C. under Ar. The reaction flask was evacuated and refilled first with Ar then with hydrogen (3×). The reaction mixture was stirred at 25° C. under hydrogen (1 atm) for 3 h, filtered through a pad of Celite and washed with hexane. The filtrate was concentrated to yield 12.6 g (57%, purity 75%) of 3-methylpent-1-en-3-ol.

A mixture of 3-methylpent-1-en-3-ol (75% wt, 12.6 g, 95 mmol), 2-methoxyprop-1-ene (18.8 g, 260 mmol) and triethanolamine phosphate (0.15 g) was added to a pressure vessel with stirrer. The autoclave was flushed and heated to 110° C. (pressure 5 bar) for 40 min. The temperature was then raised to 200° C. (pressure 20 bar) and maintained for 1 h. After cooling of the reaction mixture to 25° C. and addition of H$_2$O, the aq. layer was extracted with MTBE (2×). The org. phases were washed with brine, dried (MgSO$_4$), filtered and the filtrate was concentrated. The crude product was distilled over a Widmer column (b.p. 88° C., 26 mbar) to yield 5.49 g (41%) of 6-methyloct-5-en-2-one as a mixture of E/Z-isomers (ratio 1.5:1) as a colorless oil.

Ethyl 2-(diethoxyphosphoryl)acetate (6.1 ml, 30.6 mmol) in THF (15 ml) was added to a suspension of sodium hydride (55% wt, 1.34 g, 30.6 mmol) in THF (15 ml) at 0-5° C. After the light yellow solution was stirred at 25° C. for 30 min, 6-methyloct-5-en-2-one (3.90 g, 27.8 mmol) in THF (15 ml) was added at 0-5° C., and the mixture was stirred at 0→75° C. for 2 h. After addition of H$_2$O, the aq. layer was extracted with MTBE (2×). The org. phases were washed with H$_2$O and brine, dried (MgSO$_4$), filtered and the filtrate was concentrated. The crude product was purified by flash chromatography on SiO$_2$ (hexane/EtOAc 99:1) to yield 4.25 g (72%, purity 98%) of ethyl 3,7-dimethylnona-2,6-dienoate as a mixture of four E/Z-isomers (ratio 6:4:1.4:1) as a colorless oil.

$^{13}$C-NMR (CDCl$_3$, 100 MHz); mixture of E/Z-isomers: δ=166.8 (s), 166.8 (s), 166.3 (s), 166.3 (s), 160.1 (s), 159.9 (s), 159.7 (s), 159.7 (s), 138.2 (s), 138.0 (s), 137.7 (s), 137.5 (s), 123.3 (d), 122.6 (d), 122.0 (d), 121.4 (d), 116.2 (d), 116.2 (d), 115.6 (d), 115.6 (d), 59.4 (t), 59.4 (t), 59.4 (t), 59.4 (t), 41.2 (t), 41.0 (t), 33.7 (t), 33.4 (t), 32.3 (t), 32.3 (t), 26.6 (t), 26.4 (t), 25.9 (t), 25.7 (t), 25.3 (q), 25.3 (q), 24.7 (t), 24.7 (t), 22.8 (2q), 18.8 (2q), 15.9 (q), 15.8 (q), 14.3 (4q), 12.8 (q), 12.7 (q), 12.7 (q), 12.7 (q) ppm.

MS (EI); major isomer: 210 (1, [M]$^{+\cdot}$), 195 (1), 165 (6), 137 (9), 128 (24), 100 (13), 83 (40), 82 (10), 67 (6), 55 (100), 41 (23), 29 (8).

b) Synthesis of ethyl 2-(2-ethyl-1,2-dimethylcyclopentyl)acetate

According to Example 1 b, starting from ethyl 3,7-dimethylnona-2,6-dienoate (4.25 g, 19.9 mmol), 4.25 g (95%, purity 94%) of ethyl 2-(2-ethyl-1,2-dimethylcyclopentyl)-acetate was obtained after purification by distillation (Kugelrohr apparatus, 110° C., 0.06 torr) as a mixture of two diastereomers (ratio 1:1) as a colorless oil.

$^{13}$C-NMR (CDCl$_3$, 100 MHz); mixture of two diastereomers: δ=173.6 (s), 173.6 (s), 59.9 (t), 59.9 (t), 47.0 (s), 46.9 (s), 46.3 (s), 45.8 (s), 42.0 (t), 41.0 (t), 37.4 (t), 36.3 (t), 35.9 (t), 34.6 (t), 28.5 (t), 27.8 (t), 21.3 (q), 21.1 (q), 20.4 (q), 19.7 (q), 19.4 (t), 19.4 (t), 14.3 (2q), 9.8 (q), 9.5 (q) ppm.

MS (EI, tR=7.19 min); major isomer: 212 (1, [M]$^{+\cdot}$), 197 (1), 183 (4), 169 (7), 167 (19), 166 (69, [M]$^{+\cdot}$-EtOH), 125 (32), 124 (30), 109 (32), 98 (48), 95 (68), 88 (15), 83 (24), 69 (58), 55 (100), 43 (24), 41 (54), 29 (34).

MS (EI, tR=7.16 min); minor isomer: 212 (1, [M]$^{+\cdot}$), 197 (1), 183 (7), 169 (7), 167 (22), 166 (71, [M]$^{+\cdot}$-EtOH), 125

(33), 124 (30), 109 (29), 98 (47), 95 (86), 88 (16), 83 (25), 69 (58), 55 (100), 43 (25), 41 (55), 29 (34).

Odor description: fruity pungent, slightly woody.

c) Synthesis of ethyl 2-(2-ethyl-1,2-dimethylcyclopentyl)propanoate

According to Example 2b, starting from ethyl 2-(2-ethyl-1,2-dimethylcyclopentyl)acetate (0.98 g, 4.93 mmol), 0.94 g (75%, purity 89%) of ethyl 2-(2-ethyl-1,2-dimethylcyclopentyl)propanoate was obtained after purification by FC on $SiO_2$ (hexane/EtOAc 199:1→99:1) as a mixture of four diastereomers as a light yellow oil.

$^{13}C$-NMR ($CDCl_3$, 100 MHz); mixture of four diastereomers: δ=176.5 (s), 176.4 (s), 176.3 (s), 176.3 (s), 59.7 (t), 59.6 (t), 59.6 (t), 59.6 (t), 49.3 (s), 49.3 (s), 47.8 (s), 47.7 (s), 47.6 (s), 47.5 (s), 47.2 (s), 46.9 (s), 45.0 (d), 44.3 (d), 44.1 (d), 43.5 (d), 38.7 (t), 38.6 (t), 38.3 (t), 38.2 (t), 37.5 (t), 37.3 (t), 34.7 (t), 34.1 (t), 30.3 (t), 28.4 (t), 27.4 (t), 25.9 (t), 20.8 (q), 20.6 (q), 19.8 (q), 19.3 (t), 19.1 (t), 18.6 (q), 18.5 (t), 18.3 (t), 17.5 (2q), 16.5 (q), 16.3 (q), 15.2 (q), 15.1 (q), 14.3 (q), 14.3 (q), 14.1 (q), 14.1 (q), 13.5 (q), 13.3 (q), 10.2 (q), 10.0 (q), 9.2 (q), 9.1 (q) ppm.

MS (EI); major isomer: 126 (1, [M]$^{+\cdot}$), 211 (2), 197 (6), 183 (14), 180 (34, [M]$^{+\cdot}$-EtOH), 123 (24), 112 (31), 109 (21), 102 (100), 95 (70), 83 (41), 69 (62), 55 (86), 41 (53), 29 (27).

Odor description: fruity apple, green.

d) Synthesis of ethyl 2,3,7-trimethyldeca-2,6-dienoate

3-Methylhex-1-yn-3-ol was converted into 3-methylhex-1-en-3-ol and then into 6-methylnon-5-en-2-one as described in Example 6a.

Ethyl 2-(diethoxyphosphoryl)propanoate (5.5 ml, 25.5 mmol) in THF (13 ml) was added to a suspension of sodium hydride (55% wt, 0.62 g, 25.5 mmol) in THF (13 ml) at 0-5° C. After the light yellow solution was stirred at 25° C. for 30 min, 6-methylnon-5-en-2-one (3.58 g, 23.2 mmol) in THF (23 ml) was added at 0-5° C., and the mixture was stirred at 0→60° C. for 16 h. After addition of $H_2O$, the aq. layer was extracted with MTBE (2×). The org. phases were washed with $H_2O$ and brine, dried ($MgSO_4$), filtered and the filtrate was concentrated. The crude product was purified by flash chromatography on $SiO_2$ (hexane/EtOAc 199:1) to yield 2.64 g (48%, purity 100%) of ethyl 2,3,7-trimethyldeca-2,6-dienoate as a mixture of four E/Z-isomers (ratio 1.8:1.3:1.4:1) as a colorless oil.

$^{13}C$-NMR ($CDCl_3$, 100 MHz); mixture of E/Z-isomers: δ=170.0 (s), 170.0 (s), 169.8 (s), 169.8 (s), 146.0 (s), 146.0 (s), 145.6 (s), 145.4 (s), 136.2 (s), 136.0 (s), 135.7 (s), 135.5 (s), 124.6 (d), 124.1 (d), 123.8 (d), 123.2 (d), 123.0 (s), 123.0 (s), 122.8 (s), 122.8 (s), 60.0 (2t), 60.0 (2t), 41.8 (2t), 36.7 (t), 36.5 (t), 36.4 (t), 36.2 (t), 33.7 (2t), 27.0 (t), 26.9 (t), 25.8 (t), 25.7 (t), 23.3 (2q), 21.1 (t), 21.1 (t), 21.0 (2q), 20.9 (t), 20.9 (t), 20.2 (q), 20.2 (q), 15.9 (2q), 15.8 (q), 15.7 (q), 15.3 (q), 15.3 (q), 14.3 (3q), 14.3 (q), 14.0 (2q), 13.7 (q), 13.7 (q) ppm.

MS (EI); major isomer: 238 (1, [M]$^{+\cdot}$), 223 (1), 193 (4), 165 (6), 142 (13), 97 (28), 96 (15), 67 (7), 55 (100), 43 (7), 41 (11), 29 (5).

e) Synthesis of ethyl 2-(1,2-dimethyl-2-propylcyclopentyl)propanoate

According to Example 1b, starting from ethyl 2,3,7-trimethyldeca-2,6-dienoate (2.60 g, 10.9 mmol), 2.03 g (74%, purity 95%) of ethyl 2-(1,2-dimethyl-2-propylcyclopentyl)-propanoate was obtained after purification by FC on $SiO_2$ (hexane/EtOAc 99:1→98:2) as a mixture of four diastereomers (ratio 2:2:1:1) as a colorless oil.

$^{13}C$-NMR ($CDCl_3$, 100 MHz); mixture of four diastereomers: δ=176.5 (s), 176.4 (s), 176.4 (s), 176.3 (s), 59.7 (t), 59.7 (t), 59.6 (t), 59.6 (t), 49.4 (s), 49.3 (s), 47.7 (s), 47.6 (s), 47.6 (s), 47.4 (s), 47.0 (s), 46.9 (s), 45.0 (d), 44.3 (d), 44.1 (d), 43.5 (d), 40.8 (t), 38.8 (t), 38.5 (t), 38.4 (t), 38.3 (t), 38.2 (t), 38.1 (t), 38.0 (t), 37.9 (t), 36.5 (t), 35.6 (t), 35.0 (t), 21.6 (q), 21.4 (q), 20.6 (q), 19.5 (q), 19.4 (t), 19.2 (t), 19.1 (t), 19.0 (t), 18.6 (t), 18.5 (t), 18.1 (t), 18.0 (t), 17.4 (2q), 16.6 (q), 16.4 (q), 15.4 (q), 15.4 (q), 15.4 (q), 15.3 (q), 15.1 (q), 15.1 (q), 14.3 (q), 14.3 (q), 14.1 (q), 14.1 (q), 13.5 (q), 13.3 (q) ppm.

MS (EI, tR=7.82 min); isomer 1: 240 (1, [M]$^{+\cdot}$), 225 (2), 197 (17), 194 (25, [M]$^{+\cdot}$-EtOH), 123 (16), 112 (32), 102 (100), 95 (66), 83 (62), 69 (50), 56 (25), 55 (87), 43 (28), 41 (53), 29 (25).

MS (EI, tR=7.84 min); isomer 2: 240 (1, [M]$^{+\cdot}$), 225 (2), 197 (14), 194 (24, [M]$^{+\cdot}$-EtOH), 123 (16), 112 (34), 102 (100), 95 (34), 83 (60), 69 (47), 56 (24), 55 (84), 43 (26), 41 (50), 29 (23).

MS (EI, tR=7.98 min); isomer 3: 240 (1, [M]$^{+\cdot}$), 225 (1), 194 (19, [M]$^{+\cdot}$-EtOH), 123 (13), 112 (29), 102 (100), 95 (47), 83 (61), 69 (47), 56 (25), 55 (80), 43 (23), 41 (46), 29 (22).

MS (EI, tR=8.06 min); isomer 4: 240 (1, [M]$^{+\cdot}$), 225 (1), 194 (19, [M]$^{+\cdot}$-EtOH), 123 (13), 112 (29), 102 (100), 95 (32), 83 (59), 69 (46), 56 (25), 55 (77), 43 (23), 41 (44), 29 (21).

Odor description: fruity apple physalis, natural, green, reminiscent of damascone.

EXAMPLE 7 a) Synthesis of ethyl 2-(1,2,2-trimethylcyclopentyl)acetate

According to Example 1b, starting from ethyl 3,7-dimethylocta-2,6-dienoate (49.1 g, 250 mmol), 18.3 g (35%, purity 95%) of ethyl 2-(1,2,2-trimethylcyclopentyl)acetate was obtained after purification by distillation (Kugelrohr apparatus, 125° C., 0.07 torr) as a colorless oil.

$^1H$ NMR ($CDCl_3$, 400 MHz): δ=4.12 (q, J=7.1 Hz, 1H), 4.11 (q, J=7.1 Hz, 1H), 2.24-2.16 (m, 2H), 1.89-1.81 (m, 1H), 1.68-1.56 (m, 4H), 1.51-1.43 (m, 1H), 1.26 (t, J=7.1 Hz, 3H), 0.94 (s, 3H), 0.88 (s, 3H), 0.86 (s, 3H) ppm.

$^{13}C$-NMR ($CDCl_3$, 100 MHz): δ=173.5 (s), 59.9 (t), 45.2 (s), 43.9 (s), 41.6 (t), 39.0 (t), 36.8 (t), 24.5 (q), 23.5 (q), 21.1 (q), 19.4 (t), 14.3 (q) ppm.

MS (EI): 198 (1, [M]$^{+\cdot}$), 183 (5), 169 (1), 155 (24), 153 (45), 152 (100, [M]$^{+\cdot}$-EtOH), 111 (68), 110 (79), 109 (42), 96 (24), 95 (68), 94 (30), 88 (22), 83 (19), 82 (20), 81 (18), 69 (67), 56 (25), 55 (52), 41 (53), 29 (47).

Odor description: fruity raspberry, green acid waxy woody, fraistone.

b) Synthesis of ethyl 2-(1,2,2-trimethylcyclopentyl)butanoate

Ethyl 2-(1,2,2-trimethylcyclopentyl)acetate (2.00 g, 10.1 mmol) in THF (10 ml) was added to a solution of LDA (freshly prepared from BuLi (6.9 ml, 11.1 mmol) and diisopropylamine (1.6 ml, 11.1 mmol)) in THF (11 ml) at −78° C. The mixture was stirred at −78° C. for 30 min before iodoethane (1.2 ml, 15.1 mmol) in HMPA (2.6 ml, 15.1 mmol) was added at −78° C. The mixture was stirred at 25° C. for 3 h. After addition of sat. aq. NH$_4$Cl-solution, the aq. layer was extracted with MTBE (2×). The org. phases were dried (MgSO$_4$), filtered and the filtrate was concentrated. The residue was purified by flash chromatography on SiO$_2$ (hexane/EtOAc 199:1→99:1) to yield 1.31 g (54%, purity 95%) of ethyl 2-(1,2,2-trimethylcyclopentyl)butanoate as a mixture of two diastereomers (ratio 5.7:1) as a colorless oil.

$^1$H NMR (CDCl$_3$, 400 MHz); mixture of two diastereomers: δ=4.21-4.05 (m, 4H), 2.40 (dd, J=11.8, 3.4 Hz, 1H), 2.29 (dd, J=12.0, 3.1 Hz, 1H), 1.79-1.67 (m, 4H), 1.66-1.52 (m, 8H), 1.48-1.35 (m, 4H), 1.28 (t, J=7.1 Hz, 3H), 1.26 (t, J=7.1 Hz, 3H), 1.02 (s, 3H), 1.01 (s, 3H), 0.99 (s, 3H), 0.98 (d, J=0.6 Hz, 3H), 0.94 (s, 3H), 0.85 (t, J=7.4 Hz, 3H), 0.83 (t, J=7.7 Hz, 3H), 0.79 (s, 3H) ppm.

$^{13}$C-NMR (CDCl$_3$, 100 MHz); mixture of two diastereomers: δ=175.7 (s), 175.6 (s), 59.6 (t), 59.6 (t), 53.8 (d), 53.2 (d), 48.4 (s), 46.8 (s), 44.5 (s), 44.0 (s), 41.5 (t), 41.2 (t), 39.0 (t), 38.6 (t), 25.6 (2q), 24.5 (q), 23.2 (t), 22.9 (q), 20.9 (t), 19.2 (t), 18.5 (t), 17.4 (q), 17.2 (q), 14.4 (q), 14.2 (q), 12.7 (q), 12.6 (q) ppm.

MS (EI); mixture of two diastereomers: 226 (2, [M]$^{+\cdot}$), 211 (4), 197 (23), 183 (20), 180 (55, [M]$^{+\cdot}$-EtOH), 138 (16), 127 (25), 116 (100), 111 (24), 109 (35), 101 (23), 97 (19), 95 (30), 83 (20), 69 (41), 55 (43), 41 (31), 29 (23).

Odor description: fruity agrestic, woody ambery.

c) Synthesis of ethyl 2-(1,2,2-trimethylcyclopentyl)pentanoate

Ethyl 2-(1,2,2-trimethylcyclopentyl)acetate (2.00 g, 10.1 mmol) in THF (10 ml) was added to a solution of LDA (freshly prepared from BuLi (7.6 ml, 12.1 mmol) and diisopropylamine (1.7 ml, 12.1 mmol)) in THF (12 ml) at −78° C. The mixture was stirred at −78° C. for 40 min before 1-iodopropane (1.9 ml, 15.1 mmol) in HMPA (2.6 ml, 15.1 mmol) was added at −78° C. The mixture was stirred at 25° C. for 2 h. After addition of sat. aq. NH$_4$Cl-solution, the aq. layer was extracted with MTBE (2×). The org. phases were dried (MgSO$_4$), filtered and the filtrate was concentrated. The residue was purified by flash chromatography on SiO$_2$ (cyclohexane/EtOAc 199:1→99:1) to yield 0.98 g (39%, purity 97%) of ethyl 2-(1,2,2-trimethylcyclopentyl)pentanoate as a mixture of two diastereomers (ratio 3.5:1) as a colorless oil.

$^1$H NMR (CDCl$_3$, 400 MHz); mixture of two diastereomers: δ=4.19-4.03 (m, 4H), 2.50 (dd, J=12.1, 2.8 Hz, 1H), 2.39 (dd, J=12.0, 2.8 Hz, 1H), 1.79-1.67 (m, 4H), 1.62-1.52 (m, 8H), 1.45-1.14 (m, 8H), 1.27 (t, J=7.1 Hz, 3H), 1.25 (t, J=7.1 Hz, 3H), 1.02 (s, 6H), 1.00 (s, 3H), 0.98 (d, J=0.6 Hz, 3H), 0.95 (s, 3H), 0.90 (t, J=7.2 Hz, 3H), 0.89 (t, J=7.2 Hz, 3H), 0.79 (s, 3H) ppm.

$^{13}$C-NMR (CDCl$_3$, 100 MHz); mixture of two diastereomers: δ=175.8 (2s), 59.6 (t), 59.5 (t), 51.4 (d), 51.0 (d), 48.3 (s), 46.7 (s), 44.5 (s), 44.0 (s), 41.5 (t), 41.2 (t), 39.1 (t), 38.5 (t), 32.4 (t), 30.0 (t), 25.7 (q), 25.6 (q), 24.4 (q), 22.9 (q), 21.5 (t), 21.4 (t), 19.1 (t), 18.5 (t), 17.4 (q), 17.2 (q), 14.4 (q), 14.2 (q), 14.1 (q), 14.1 (q) ppm.

MS (EI); mixture of two diastereomers: 240 (2, [M]$^{+\cdot}$), 225 (3), 197 (41), 194 (43, [M]$^{+\cdot}$ EtOH), 152 (20), 130 (100), 127 (20), 123 (24), 111 (34), 109 (28), 101 (61), 95 (28), 81 (16), 69 (49), 55 (50), 41 (32), 29 (27).

Odor description: fruity agrestic, strawberry, apple.

EXAMPLE 8: SYNTHESIS OF ETHYL 2-(1-ETHYL-2,2-DIMETHYLCYCLOPENTYL)PROPANOATE a) Synthesis of ethyl 3-ethyl-2,7-dimethylocta-2,6-dienoate

According to Example 1a, starting from 7-methyloct-6-en-3-one (prepared by methods known to the person skilled in the art) (2.80 g, 20.0 mmol), 1.16 g (25%, purity 98%) of ethyl 3-ethyl-2,7-dimethylocta-2,6-dienoate was obtained after purification by FC on SiO$_2$ (hexane/EtOAc 99:1) (mixture of E/Z-isomers; ratio 1.3:1) as a colorless oil.

$^1$H NMR (CDCl$_3$, 400 MHz); mixture of E/Z-isomers: δ=5.16-5.10 (m, 2H), 4.18 (q, J=7.2 Hz, 2H), 4.17 (q, J=7.2 Hz, 2H), 2.34-2.29 (m, 4H), 2.17-2.05 (m, 8H), 1.86 (br. s, 6H), 1.69 (q, J=0.9 Hz, 3H), 1.68 (br. q, J=1.0 Hz, 3H), 1.61 (br. s, 6H), 1.30 (t, J=7.2 Hz, 3H), 1.29 (t, J=7.2 Hz, 3H), 1.05 (t, J=7.5 Hz, 3H), 1.02 (t, J=7.6 Hz, 3H) ppm.

$^{13}$C-NMR (CDCl$_3$, 100 MHz); mixture of E/Z-isomers: δ=170.0 (2s), 151.0 (s), 150.9 (s), 132.2 (s), 131.7 (s), 124.1 (d), 123.7 (d), 122.8 (s), 122.8 (s), 60.0 (2t), 34.0 (t), 33.3 (t), 27.5 (t), 27.4 (t), 26.7 (t), 26.3 (t), 25.7 (2q), 17.6 (q), 17.6 (q), 15.4 (q), 15.3 (q), 14.3 (q), 14.3 (q), 13.3 (q), 12.1 (q) ppm.

MS (EI, tR=7.40 min); major isomer: 224 (4, [M]$^{+\cdot}$), 179 (27, [M]$^{+\cdot}$-Eta), 156 (22), 151 (27), 150 (16), 141 (17), 127 (21), 123 (17), 113 (16), 110 (46), 109 (14), 69 (100), 67 (17), 53 (11), 41 (50), 29 (14).

MS (EI, tR=7.32 min); minor isomer: 224 (4, [M]$^{+\cdot}$), 179 (21, [M]$^{+\cdot}$-Eta), 156 (35), 151 (43), 150 (20), 141 (21), 127 (30), 123 (17), 113 (24), 110 (66), 109 (22), 69 (100), 67 (21), 53 (13), 41 (58), 29 (19).

b) Synthesis of ethyl 2-(1-ethyl-2,2-dimethylcyclopentyl)propanoate

According to Example 1 b, starting from ethyl 3-ethyl-2,7-dimethylocta-2,6-dienoate (1.16 g, 5.17 mmol), 0.70 g (57%, purity 96%) of ethyl 2-(1-ethyl-2,2-dimethylcyclopentyl)propanoate was obtained after purification by FC on SiO$_2$ (hexane/EtOAc 99:1) as a mixture of two diastereomers (ratio 2.1:1) as a colorless oil.

$^{13}$C-NMR (CDCl$_3$, 100 MHz); mixture of two diastereomers: δ=177.3 (s), 176.6 (s), 59.9 (t), 59.7 (t), 50.8 (s), 50.4 (s), 45.7 (s), 45.4 (s), 44.6 (d), 43.7 (d), 42.2 (t), 41.9 (t), 33.5 (t), 33.3 (t), 26.3 (q), 26.1 (q), 25.4 (q), 24.7 (t), 24.3 (t), 23.8 (q), 20.2 (t), 19.8 (t), 16.2 (q), 14.1 (q), 14.1 (q), 13.7 (q), 11.2 (q), 9.9 (q) ppm.

MS (EI, tR=7.43 min); major isomer: 226 (1, [M]$^{+\cdot}$), 211 (4), 197 (11), 180 (25, [M]$^{+\cdot}$ EtOH), 155 (8), 141 (18), 125 (25), 124 (20), 123 (25), 109 (26), 102 (100), 95 (38), 83 (31), 74 (13), 69 (48), 55 (38), 41 (28), 29 (23).

MS (EI, tR=7.41 min); minor isomer: 226 (1, [M]$^{+\cdot}$), 211 (3), 197 (12), 180 (23, [M]$^{+\cdot}$ EtOH), 155 (8), 141 (14), 125 (25), 124 (17), 123 (22), 109 (25), 102 (100), 95 (35), 83 (27), 74 (14), 69 (41), 55 (34), 41 (27), 29 (23).

Odor description: fruity, red fruits, cherry, plumy, slightly woody.

EXAMPLE 9: SYNTHESIS OF ETHYL 2-(1,2-DIMETHYLCYCLOPENTYL)PROPANOATE

Pd/C (5 wt %, 0.2 g) was added to a solution of ethyl 2-(1-methyl-2-methylene-cyclopentyl)propanoate (Example 5a) (1.86 g, 9.46 mmol) in EtOH (40 ml) at 25° C. under Ar.

The reaction flask was evacuated and refilled first with Ar then with hydrogen (3×). The reaction mixture was stirred at 25° C. under hydrogen (1 atm) for 2 h, filtered through a pad of Celite and washed with EtOH. The filtrate was concentrated and 1.33 g (70%, purity 98%) of ethyl 2-(1,2-dimethylcyclopentyl)propanoate was obtained after purification by FC on $SiO_2$ (hexane/EtOAc 99:1→98:2) as a mixture of two diastereomers (ratio 8:1) as a colorless oil.

$^{13}$C-NMR (CDCl$_3$, 100 MHz); major isomer: δ=176.4 (s), 59.8 (t), 47.4 (d), 45.1 (s), 39.9 (d), 36.7 (t), 32.8 (t), 21.4 (t), 18.1 (q), 14.3 (q), 14.3 (q), 12.9 (q) ppm.

MS (EI); major isomer: 198 (1, [M]$^{+\cdot}$), 183 (2), 153 (5, [M]$^{+\cdot}$-EtOH), 141 (3), 125 (11), 102 (100), 97 (19), 83 (8), 81 (7), 74 (16), 69 (15), 55 (21), 45 (2), 41 (14), 29 (11).

Odor description: fruity agrestic, strawberry peppery.

EXAMPLE 10: SYNTHESIS OF VARIOUS NITRILES a) Synthesis of 2-(1,2,2-trimethylcyclopentyl)acetonitrile

According to Example 1 b, starting from 3,7-dimethylocta-2,6-dienenitrile (14.9 g, 100 mmol), 14.4 g (92%, purity 97%) of 2-(1,2,2-trimethylcyclopentyl)acetonitrile was obtained after purification by distillation (Kugelrohr apparatus, 120° C., 0.07 torr) as a white solid.

$^1$H NMR (CDCl$_3$, 400 MHz): δ=2.30-2.20 (m, 2H), 1.84-1.76 (m, 1H), 1.69-1.60 (m, 4H), 1.58-1.50 (m, 1H), 1.08 (s, 3H), 0.94 (s, 3H), 0.90 (s, 3H) ppm.

$^{13}$C-NMR (CDCl$_3$, 100 MHz): δ=119.5 (s), 45.0 (s), 43.2 (s), 39.3 (t), 37.1 (t), 25.8 (t), 24.2 (q), 24.0 (q), 21.4 (q), 19.0 (t) ppm.

MS (EI): 151 (2, [M]$^{+\cdot}$), 150 (14), 136 (76), 122 (30), 111 (21), 109 (30), 108 (61), 96 (19), 95 (57), 94 (40), 83 (21), 82 (17), 81 (17), 70 (50), 69 (72), 67 (23), 56 (35), 55 (100), 41 (70), 39 (33), 29 (11), 27(14).

Odor description: agrestic green bornyl minty, fatty citrus Citral-like.

b) Synthesis of 2-(1,2,2-trimethylcyclopentyl)propanenitrile

According to Example 2b, starting from 2-(1,2,2-trimethylcyclopentyl)acetonitrile (7.56 g, 50.0 mmol), 7.30 g (88%, purity 100%) of 2-(1,2,2-trimethylcyclopentyl)propanenitrile was obtained after purification by distillation (Kugelrohr apparatus, 150° C., 0.06 torr) as a mixture of two diastereomers as a light yellow solid.

$^1$H NMR (CDCl$_3$, 400 MHz); mixture of two diastereomers: δ=2.77 (q, J=7.1 Hz, 1H), 2.63 (q, J=7.1 Hz, 1H), 1.88-1.44 (m, 12H), 1.29 (d, J=7.1 Hz, 3H), 1.28 (d, J=7.3 Hz, 3H), 1.14 (s, 3H), 1.05 (s, 3H), 1.02 (s, 3H), 0.99 (s, 3H), 0.98 (s, 3H), 0.94 (s, 3H) ppm.

$^{13}$C-NMR (CDCl$_3$, 100 MHz); mixture of two diastereomers: δ=123.2 (s), 122.6 (s), 46.7 (s), 46.5 (s), 43.9 (s), 43.4 (s), 41.9 (t), 40.9 (t), 39.9 (t), 37.2 (t), 33.7 (d), 30.9 (d), 25.0 (q), 24.9 (q), 24.7 (q), 23.6 (q), 19.0 (t), 18.3 (t), 17.9 (2q), 15.3 (q), 14.2 (q) ppm.

MS (EI, tR=6.07 min); major isomer: 165 (2, [M]$^{+\cdot}$), 164 (6), 150 (52), 123 (21), 111 (27), 108 (91), 95 (57), 82 (21), 70 (42), 69 (88), 67 (20), 56 (24), 55 (100), 41 (58), 39 (24), 29 (10), 27(11).

MS (EI, tR=6.21 min); minor isomer: 165 (2, [M]$^{+\cdot}$), 164 (6), 150 (47), 123 (20), 111 (40), 108 (83), 95 (51), 82 (19), 70 (38), 69 (93), 67 (19), 56 (24), 55 (100), 53 (18), 41 (56), 39 (23), 29 (10), 27(10).

Odor description: agrestic fruity, ketonic.

d) Synthesis of 2-(2-ethyl-1,2-dimethylcyclopentyl)acetonitrile

According to Example 1 b, starting from 3,7-dimethylnona-2,6-dienenitrile (4.08 g, 25 mmol), 2.65 g (62%, purity 97%) of 2-(2-ethyl-1,2-dimethylcyclopentyl)acetonitrile was obtained after purification by FC on $SiO_2$ (hexane/EtOAc 99:1→98:2) as a mixture of two diastereomers (ratio 1:1) as a colorless oil.

$^{13}$C-NMR (CDCl$_3$, 100 MHz); mixture of two diastereomers: δ=119.6 (s), 119.4 (s), 46.1 (s), 46.1 (s), 46.0 (s), 45.4 (s), 37.5 (t), 37.0 (t), 35.9 (t), 35.5 (t), 28.4 (t), 28.2 (t), 25.8 (t), 25.5 (t), 21.5 (q), 21.3 (q), 20.2 (q), 20.1 (q), 19.0 (t), 18.9 (t), 9.5 (q), 9.4 (q) ppm.

MS (EI, tR=6.50 min); isomer 1: 165 (1, [M]$^{+\cdot}$), 164 (4), 150 (41), 136 (38), 122 (37), 109 (13), 108 (16), 95 (79), 83 (23), 70 (18), 69 (45), 67 (19), 56 (24), 55 (100), 53 (21), 41 (53), 39 (21), 29 (11), 27(10).

MS (EI, tR=6.52 min); isomer 2: 165 (1, [M]$^{+\cdot}$), 164 (6), 150 (53), 136 (46), 122 (44), 109 (18), 108 (18), 95 (84), 83 (22), 70 (21), 69 (51), 67 (22), 56 (27), 55 (100), 53 (22), 41 (56), 39 (23), 29 (12), 27(10).

Odor description: citrus green agrestic, minty, fruity.

EXAMPLE 11 a) Synthesis of ethyl 2-(2,2-dimethylcyclopentyl)propanoate

According to Example 1 b, starting from (E)-ethyl 2,7-dimethylocta-2,6-dienoate (prepared from 5-methylhex-4-enal by methods known to the person skilled in the art) (2.66 g, 13.6 mmol), 1.78 g (58%, purity 88%) of ethyl 2-(2,2-dimethylcyclopentyl)propanoate was obtained after purification by FC on $SiO_2$ (hexane/EtOAc 99:1→98:2) as a mixture of two diastereomers (ratio 9:1) as a colorless oil. Further purification yielded 0.47 g (purity 93%) of the two diastereomers (ratio 15:1) of ethyl 2-(2,2-dimethylcyclopentyl)-propanoate.

$^{13}$C-NMR (CDCl$_3$, 100 MHz); major isomer: δ=177.0 (s), 59.9 (t), 51.9 (d), 43.8 (t), 42.1 (d), 40.6 (s), 30.1 (t), 30.1 (q), 21.7 (q), 21.1 (t), 17.4 (q), 14.2 (q) ppm.

MS (EI); major isomer: 198 (2, [M]$^{+\cdot}$), 183 (6, [M]$^{+\cdot}$—CH$_3$), 152 (55, [M]$^{+\cdot}$-EtOH), 125 (22), 124 (18), 115 (11), 109 (24), 102 (100), 95 (13), 83 (16), 82 (21), 81 (18), 74 (20), 69 (40), 55 (40), 41 (31), 29 (25).

Odor description: fruity, winey, fatty, floral.

b) Synthesis of ethyl 2-(2,2-dimethylcyclopentyl)acetate

According to Example 1b, starting from (E)-ethyl 7-methylocta-2,6-dienoate (prepared from 5-methylhex-4-enal by methods known to the person skilled in the art) (5.51 g, 30.2 mmol), 5.43 g (88%, purity 90%) of ethyl 2-(2,2-dimethylcyclopentyl)acetate was obtained. Purification by FC on $SiO_2$ (hexane/EtOAc 99:1→98:2) yielded 1.73 g (30%, purity 96%) of ethyl 2-(2,2-dimethylcyclopentyl)acetate as a colorless oil.

$^1$H NMR (CDCl$_3$, 400 MHz): δ=4.12 (q, J=7.2 Hz, 2H), 2.36 (dd, J=14.5, 4.1 Hz, 1H), 2.36 (dd, J=14.6, 10.4 Hz, 1H), 1.98-1.81 (m, 2H), 1.62-1.55 (m, 2H), 1.46-1.39 (m, 2H), 1.38-1.29 (m, 1H), 1.25 (t, J=7.2 Hz, 3H), 0.98 (s, 3H), 0.75 (s, 3H) ppm.

¹³C-NMR (CDCl₃, 100 MHz): δ=174.0 (s), 60.1 (t), 45.9 (d), 41.4 (t), 40.5 (s), 35.5 (t), 30.4 (t), 27.7 (q), 21.7 (q), 21.0 (t), 14.2 (q) ppm.

MS (EI): 184 (2, [M]⁺·), 169 (6, [M]⁺·-CH₃), 142 (15), 141 (33), 139 (50), 138 (100, [M]⁺·-EtOH), 129 (11), 123 (12), 111 (18), 110 (39), 101 (15), 96 (25), 95 (45), 88 (28), 82 (24), 81 (29), 70 (20), 69 (43), 67 (15), 56 (16), 55 (43), 45 (4), 43 (15), 41 (37), 29 (24).

Odor description: fruity red fruits, slightly winey.

c) Synthesis of ethyl 2-(2,2-dimethylcyclopentyl)propanoate

According to Example 2b, starting from ethyl 2-(2,2-dimethylcyclopentyl)acetate (1.72 g, 9.33 mmol), ethyl 2-(2,2-dimethylcyclopentyl)propanoate was obtained as a mixture of two diastereomers (ratio 3.5:1; the major diastereomer of this example corresponds to the minor diastereomer of example 11a.) as a light yellow oil. Olfactive purification by FC on SiO₂ (hexane/EtOAc 99:1→98:2) yielded 1.37 g (65%, purity 88%) and 0.06 g (3%, purity 95%) of the major isomer of ethyl 2-(2,2-dimethylcyclopentyl) propanoate as a colorless oil.

¹H NMR (CDCl₃, 400 MHz); major isomer: δ=4.16-4.07 (m, 2H), 2.33-2.25 (m, 1H), 1.93-1.85 (m, 1H), 1.75 (td, J=10.6, 8.1 Hz, 1H), 1.59-1.30 (m, 5H), 1.27 (t, J=7.2 Hz, 3H), 1.12 (d, J=7.0 Hz, 3H), 0.91 (s, 3H), 0.84 (s, 3H) ppm.

¹³C-NMR (CDCl₃, 100 MHz); major isomer: δ=177.2 (s), 59.9 (t), 51.7 (d), 43.2 (t), 41.0 (d), 40.5 (s), 29.2 (t), 28.2 (q), 21.6 (q), 20.3 (t), 17.7 (q), 14.1 (q) ppm.

MS (EI); major isomer: 198 (3, [M]⁺·), 183 (11, [M]⁺·—CH₃), 155 (73), 153 (25), 152 (92, [M]⁺·-EtOH), 127 (28), 125 (36), 124 (30), 115 (19), 109 (52), 102 (100), 95 (26), 83 (28), 82 (40), 81 (34), 74 (21), 70 (23), 69 (73), 67 (27), 55 (79), 41 (67), 29 (51).

¹³C-NMR and MS data for minor isomer see Example 11a above.

Odor description (major isomer): fruity red fruits, strawberry, rosy physalis, slightly winey.

EXAMPLE 12 a) Synthesis of ethyl 2-(2,2-dimethylcyclohexyl)propanoate

Hydrogen chloride (2M in H₂O, 5.3 ml, 10.5 mmol) was added to a solution of 1-methoxy-6-methylhepta-1,5-diene (prepared from 5-methylhex-4-enal by methods known to the person skilled in the art) (14.7 g, 105 mmol) in THF (250 ml) at 0° C. and the reaction mixture was stirred at 0° C. for 7 h. After addition of 2M aq. NaOH-solution, the aq. layer was extracted with MTBE. The org. phases were washed with H₂O and brine, dried (MgSO₄), filtered and the filtrate was concentrated to yield 15.9 g (83%, purity 69%) of 6-methylhept-5-enal as a yellow oil.

Ethyl 2-(diethoxyphosphoryl)propanoate (1.98 g, 8.33 mmol) in DME/NMP (4 ml, 3:1) was added to a suspension of sodium hydride (50% wt, 0.38 g, 7.88 mmol) in DME (3 ml) at 25-50° C. After the yellow suspension was stirred at 25° C. for 30 min, 6-methylhept-5-enal (0.95 g, 7.50 mmol) in DME (1 ml) was added at 15-20° C. The reaction mixture was stirred at 25° C. for 1 h, water was added and the aq. layer was extracted with MTBE (2×). The org. phases were washed with H₂O and brine, dried (MgSO₄), filtered and the filtrate was concentrated to yield 1.77 g (quant., purity 90%) of ethyl 2,8-dimethylnona-2,7-dienoate (mixture of E/Z-isomers; ratio 2.2:1).

According to Example 1 b, starting from purified (E)-ethyl 2,8-dimethylnona-2,7-dienoate (0.50 g, 2.38 mmol), 0.49 g (79%, purity 81%) of ethyl 2-(2,2-dimethylcyclohexyl)propanoate was obtained as a mixture of two diastereomers (ratio 12:1). An olfactive pure sample was obtained by purification by FC on SiO₂ (Biotage Isolera™, hexane/EtOAc 100:0→9:1) as a colorless oil.

¹³C-NMR (CDCl₃, 100 MHz); major isomer: δ=176.4 (s), 59.8 (t), 52.2 (d), 43.3 (t), 39.2 (d), 34.4 (s), 30.9 (q), 27.3 (t), 24.0 (t), 22.3 (t), 19.8 (q), 19.0 (q), 14.1 (q) ppm.

MS (EI); major isomer: 212 (1, [M]⁺·), 197 (1, [M]⁺·—CH₃), 167 (5, [M]⁺·-EtO·), 151 (4), 139 (3), 123 (9), 111 (5), 102 (100), 95 (9), 83 (11), 74 (14), 69 (20), 55 (17), 41 (19), 29 (17).

Odour description: fruity, red fruits, woody ambery, plumy, orris, irone effect.

b) Synthesis of ethyl 2-(1,2,2-trimethylcyclohexyl)acetate

Ethyl 2-(diethoxyphosphoryl)acetate (4.61 g, 20.6 mmol) in DME/NMP (12 ml, 3:1) was added to a suspension of sodium hydride (50% wt, 0.93 g, 19.5 mmol) in DME (9 ml) at 25-50° C. After the yellow suspension was stirred at 25° C. for 30 min, 7-methyloct-6-en-2-one (prepared from 6-methylhept-5-enal by methods known to the person skilled in the art) (2.60 g, 18.5 mmol) in DME (3 ml) was added at 25° C. The reaction mixture was stirred at 25° C. for 1 h, water was added and the aq. layer was extracted with MTBE (2×). The org. phases were washed with H₂O and brine, dried (MgSO₄), filtered and the filtrate was concentrated. Purification by distillation (Kugelrohr apparatus, 150° C., 0.07 torr) yielded 2.25 g (47%, purity 81%) of ethyl 3,8-dimethylnona-2,7-dienoate (mixture of E/Z-isomers; ratio 2.1:1; the impurity corresponds to (E/Z)-ethyl 3,8-dimethylnona-3,7-dienoate).

According to Example 1 b, starting from further purified ethyl 3,8-dimethylnona-2,7-dienoate (0.61 g, 2.78 mmol), 0.43 g (53%, purity 73%) of ethyl 2-(1,2,2-trimethylcyclohexyl)acetate was obtained after purification by FC on SiO₂ (Biotage Isolera™, hexane/EtOAc 100:0→9:1) as a colorless oil.

¹³C-NMR (CDCl₃, 100 MHz): δ=173.4 (s), 59.8 (t), 41.2 (t), 38.3 (s), 37.1 (t), 35.8 (s), 33.3 (t), 24.6 (q), 24.1 (q), 22.1 (2t), 20.5 (q), 14.3 (q) ppm.

MS (EI): 212 (3, [M]⁺·), 197 (2, [M]⁺·—CH₃), 167 (25), 166 (36, [M]⁺·-EtOH), 151 (37), 125 (100), 124 (50), 109 (49), 95 (18), 88 (47), 83 (28), 69 (74), 55 (57), 41 (59), 29 (53).

Odour description: fruity, red fruits, agrestic, piney.

c) Synthesis of ethyl 2-(1,2,2-trimethylcyclohexyl)propanoate

According to Example 2b, starting from ethyl 2-(1,2,2-trimethylcyclohexyl)acetate (0.30 g, purity 68%, 0.96 mmol), 0.31 g (78%, purity 55%) of ethyl 2-(1,2,2-trimethylcyclohexyl)propanoate was obtained as a mixture of two diastereomers. Purification by FC on SiO₂ (Biotage Isolera™, hexane/EtOAc 100:0→9:1) yielded 0.13 g (41%, purity 69%) of ethyl 2-(1,2,2-trimethylcyclohexyl)propanoate a mixture of two diastereomers (ratio 1.5:1) as a colorless oil.

¹³C-NMR (CDCl₃, 100 MHz); mixture of two diastereomers: δ=177.5 (s), 177.0 (s), 59.8 (t), 59.7 (t), 45.3 (d), 44.1 (d), 40.7 (s), 40.3 (s), 39.0 (t), 38.8 (t), 36.9 (s), 36.8 (s), 33.1 (t), 32.7 (t), 26.6 (q), 26.2 (q), 23.5 (q), 22.6 (q), 22.1 (t), 22.1 (2t), 21.7 (t), 17.1 (q), 15.7 (q), 15.4 (q), 14.2 (q), 14.1 (q), 14.0 (q) ppm.

MS (EI); mixture of two diastereomers: 226 (3, [M]⁺·), 211 (3, [M]⁺—CH₃), 180 (9, [M]⁺· EtOH), 125 (27), 123 (11), 109 (13), 102 (100), 97 (11), 83 (22), 81 (10), 74 (12), 69 (53), 67 (12), 57 (17), 56 (10), 55 (31), 43 (12), 41 (32), 29 (28).

Odour description: fruity agrestic, woody ambery, myraldyl effect.

EXAMPLE 13: PREPARATION OF A FEMININE FLORAL FINE FRAGRANCE

| Compound/Ingredient | parts by weight 1/1000 |
|---|---|
| 2-Methyl-1-phenylpropan-2-yl acetate (Dimethyl benzyl carbinyl acetate) | 100 |
| (E)-2-benzylideneoctanal (Hexyl cinnamic aldehyde) | 200 |
| cis-3-Hexenyl benzoate | 2 |
| 3,7-Dimethyloct-6-en-1-ol (Citronellol) | 110 |
| 6-Pentyltetrahydro-2H-pyran-2-one (Decalactone delta) (at 10% in DEP) | 4 |
| 3-(3-Isopropylphenyl)butanal (Florhydral) | 2 |
| 3,7-Dimethyloct-6-en-1-yl formate (Citronellyl formate) | 10 |
| cis-3-Hexenol | 10 |
| Indole (at 1% in TEC) | 60 |
| 3-(4-(tert-Butyl)phenyl)-2-methylpropanal (Lilial) | 60 |
| 3,7-Dimethylocta-1,6-dien-3-ol (Linalool) | 80 |
| 6-Methylhept-5-en-2-one | 2 |
| Hexyl 2-hydroxybenzoate (Hexyl Salicylate) | 50 |
| (E)-4-Methyldec-3-en-5-ol (Undecavertol) | 120 |
| Methyl-2-((3-(4-(tert-butyl)phenyl)-2-methylprop-1-en-1-yl)amino)benzoate (Verdantiol) | 10 |
| Dipropylene glycol (DPG) | 150 |
| Ethyl 2-(1,2,2-trimethylcyclopentyl)propanoate (Example 1b) | 30 |
| Total: | 1000 |

This soft floral accord with a clear linden blossom character is best to be assessed at 5 weight % in alcohol. The addition of ethyl 2-(1,2,2-trimethylcyclopentyl)propanoate impacts the top note by providing a fresh fruity effect. Ethyl 2-(1,2,2-trimethylcyclopentyl)propanoate combines well with the watery muguet elements and adds a soft fruity watermelon aspect.

EXAMPLE 14: PREPARATION OF A UNISEX MUSK ACCORD

| Compound/Ingredient | parts by weight 1/1000 |
|---|---|
| Geranyl acetate | 10 |
| Phenyl ethyl alcohol | 60 |
| Ambermax ™* (at 10% in TEC) | 50 |
| (3aR,5aS,9aS,9bR)-3a,6,6,9a-Tetramethyldodecahydro-naphtho[2,1-b]furan (Ambrofix) | 10 |
| 1,4-Dioxacycloheptadecane-5,17-dione (Brassylate Ethylene) | 320 |
| 3,7-Dimethylocta-2,6-dienal (Citral Lemarome N) | 1 |
| (E)-1-(2,6,6-Trimethylcyclohexa-1,3-dien-1-yl)but-2-en-1-one (Damascenone) | 2 |
| 4,6,6,7,8,8-Hexamethyl-1,3,4,6,7,8-hexahydro-cyclopenta[g]isochromene (Galaxolide) | 250 |
| Methyl 2-(3-oxo-2-pentylcyclopentyl)acetate (Hedione) | 60 |

| Compound/Ingredient | parts by weight 1/1000 |
|---|---|
| (1-Methyl-2-[(-1,2,2-trimethylbicyclo[3.1.0]hexan-3-yl)methyl]cyclopropyl)methanol (Javanol) | 5 |
| 3-Methyl-5-phenylpentan-1-ol (Mefrosol) | 50 |
| 4-Methyl-2-(2-methylprop-1-enyl)tetrahydro-2H-pyran (Rose Oxide CO) (at 10% in DEP) | 2 |
| Oxacyclohexadecan-2-one (Thibetolide) | 150 |
| Ethyl 2-(1,2,2-trimethylcyclopentyl)propanoate (Example 1b) | 30 |
| Total: | 1000 |

*Ambermax ™ (mixture of 2-(1,1,5,5-tetramethyl-1,3,4,5,6,7-hexahydro-2H-2,4a-methanonaphthalen-8-yl)propan-1-ol and 2-(1,1,5,5-tetramethyl-1,3,4,5,6,8a-hexahydro-2H-2,4a-methanonaphthalen-8-yl)propan-1-ol)

This soft musky rosy accord with a strong dry woody ambery facet is best to be assessed at 5 weight % in alcohol. The addition of ethyl 2-(1,2,2-trimethylcyclopentyl)-propanoate covers the impacting dry ambery note. Ethyl 2-(1,2,2-trimethylcyclopentyl)-propanoate combines well with the rose to provide a bright fruity effect with appR1 and plum facets.

The invention claimed is:

1. A method comprising using as a fragrance alone or combining with a base material in a fragranced article, a compound of formula (I)

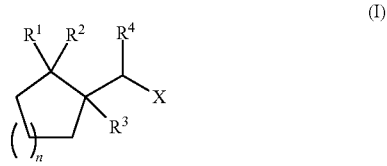

wherein
n is 1 or 2;
R¹ and R² are independently selected from the group consisting of hydrogen, methyl, ethyl, and C₃-C₅ alkyl; or
R¹ and R² form together with the carbon atom to which they are attached C₃-C₆ cycloalkyl; or
R¹ and R² form together methylidene;
R³ is selected from hydrogen, and C₁-C₃ alkyl;
R⁴ is selected from hydrogen, and C₁-C₃ alkyl; and
X is CN; or
X is —C(O)OR⁵, wherein R⁵ is selected from the group consisting of methyl, ethyl, C₃-C₅ alkyl, vinyl and C₃-C₅ alkenyl;
with the proviso that
a) at least two of the residues R¹, R² and R³ are not hydrogen;
b) when R³ is hydrogen, R⁴ is selected from C₁-C₃ alkyl;
c) when X is —CN, and R¹, R² and R³ are methyl, then R⁴ is not hydrogen.

2. The method according to claim 1 wherein the compound of formula (I) is selected from the group consisting of
ethyl 2-(1,2,2-trimethylcyclopentyl)propanoate,
methyl 2-(1,2,2-trimethylcyclopentyl)acetate,
methyl 2-(1,2,2-trimethylcyclopentyl)propanoate,
propyl 2-(1,2,2-trimethylcyclopentyl)propanoate,
isopropyl 2-(1,2,2-trimethylcyclopentyl)propanoate,
but-3-en-1-yl 2-(1,2,2-trimethylcyclopentyl)propanoate, isobutyl 2-(1,2,2-trimethylcyclopentyl)propanoate,
allyl 2-(1,2,2-trimethylcyclopentyl)propanoate,
methyl 2-(1-methylspiro[4.4]nonan-1-yl)acetate,
methyl 2-(1-methylspiro[4.4]nonan-1-yl)propanoate,
ethyl 2-(1-methylspiro[4.4]nonan-1-yl)acetate,
ethyl 2-(1-methylspiro[4.4]nonan-1-yl)propanoate,
ethyl 2-(1-methyl-2-methylenecyclopentyl)propanoate,
ethyl 2-(4-methylspiro[2.4]heptan-4-yl)propanoate,
ethyl 2-(2-ethyl-1,2-dimethylcyclopentyl)acetate,
ethyl 2-(2-ethyl-1,2-dimethylcyclopentyl)propanoate,
ethyl 2-(1,2-dimethyl-2-propylcyclopentyl)propanoate,
ethyl 2-(1,2,2-trimethylcyclopentyl)acetate,
ethyl 2-(1,2,2-trimethylcyclopentyl)butanoate,
ethyl 2-(1,2,2-trimethylcyclopentyl)pentanoate,
ethyl 2-(1-ethyl-2,2-dimethylcyclopentyl)propanoate,
ethyl 2-(1,2-dimethylcyclopentyl)propanoate,
2-(1,2,2-trimethylcyclopentyl)propanenitrile,
2-(2-ethyl-1,2-dimethylcyclopentyl)acetonitrile,
ethyl 2-(2,2-dimethylcyclopentyl)propanoate,
ethyl 2-(2,2-dimethylcyclohexyl)propanoate,
ethyl 2-(1,2,2-trimethylcyclohexyl)acetate, and
ethyl 2-(1,2,2-trimethylcyclohexyl)propanoate.

3. A fragranced article comprising as odorant a compound of formula (I),

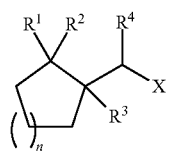

(I)

wherein
n is 1 or 2;
$R^1$ and $R^2$ are independently selected from the group consisting of hydrogen, methyl, ethyl, and $C_3$-$C_5$ alkyl; or
$R^1$ and $R^2$ form together with the carbon atom to which they are attached $C_3$-$C_6$ cycloalkyl; or
$R^1$ and $R^2$ form together methylidene;
$R^3$ is selected from hydrogen, and $C_1$-$C_3$ alkyl;
$R^4$ is selected from hydrogen, and $C_1$-$C_3$ alkyl; and
X is —CN; or
X is —C(O)$OR^5$, wherein $R^5$ is selected from the group consisting of methyl, ethyl, $C_3$-$C_5$ alkyl, vinyl and $C_3$-$C_5$ alkenyl;
with the proviso that
 a) at least two of the residues $R^1$, $R^2$ and $R^3$ are not hydrogen;
 b) when $R^3$ is hydrogen, $R^4$ is selected from $C_1$-$C_3$ alkyl;
 c) when X is —CN, and $R^1$, $R^2$ and $R^3$ are methyl, then $R^4$ is not hydrogen;
or a mixture thereof, and a consumer product base.

4. The fragranced article according to claim 3 wherein the consumer product base is selected from the group consisting of fine perfumery, household products, laundry products, body care products, cosmetic and air care products.

5. A method of improving, enhancing or modifying a consumer product base by means of addition thereto of an olfactory acceptable amount of a compound of formula (I),

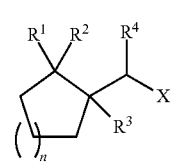

(I)

wherein
n is 1 or 2;
$R^1$ and $R^2$ are independently selected from the group consisting of hydrogen, methyl, ethyl, and $C_3$-$C_5$ alkyl; or
$R^1$ and $R^2$ form together with the carbon atom to which they are attached $C_3$-$C_6$ cycloalkyl; or
$R^1$ and $R^2$ form together methylidene;
$R^3$ is selected from hydrogen, and $C_1$-$C_3$ alkyl;
$R^4$ is selected from hydrogen, and $C_1$-$C_3$ alkyl; and
X is —CN; or
X is —C(O)$OR^5$, wherein $R^5$ is selected from the group consisting of methyl, ethyl, $C_3$-$C_5$ alkyl, vinyl and $C_3$-$C_5$ alkenyl;
with the proviso that
 a) at least two of the residues $R^1$, $R^2$ and $R^3$ are not hydrogen;
 b) when $R^3$ is hydrogen, $R^4$ is selected from $C_1$-$C_3$ alkyl;
 c) when X is —CN, and $R^1$, $R^2$ and $R^3$ are methyl, then $R^4$ is not hydrogen.

6. A compound of formula (I),

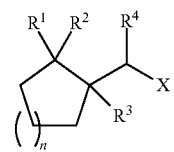

(I)

wherein
n is 1 or 2;
$R^1$ and $R^2$ are independently selected from the group consisting of hydrogen, methyl, ethyl, and $C_3$-$C_5$ alkyl; or
$R^1$ and $R^2$ form together with the carbon atom to which they are attached $C_3$-$C_6$ cycloalkyl;
$R^3$ is selected from hydrogen, and $C_1$-$C_3$ alkyl;
$R^4$ is selected from hydrogen, and $C_1$-$C_3$ alkyl; and
X is —CN; or
X is —C(O)$OR^5$, wherein $R^5$ is selected from the group consisting of methyl, ethyl, $C_3$-$C_5$ alkyl, vinyl and $C_3$-$C_5$ alkenyl;
with the proviso that
 a) at least two of the residues $R^1$, $R^2$ and $R^3$ are not hydrogen;
 b) when $R^3$ is hydrogen, $R^4$ is selected from $C_1$-$C_3$ alkyl;
 c) when X is —CN, and $R^1$, $R^2$ and $R^3$ are methyl, then $R^4$ is not hydrogen;
 d) when n is 2; $R^1$ and $R^2$ are not hydrogen.

7. The compound according to claim 6 selected from the group consisting of
ethyl 2-(1,2,2-trimethylcyclopentyl)propanoate,
methyl 2-(1,2,2-trimethylcyclopentyl)acetate,
methyl 2-(1,2,2-trimethylcyclopentyl)propanoate, propyl 2-(1,2,2-trimethylcyclopentyl)propanoate,
isopropyl 2-(1,2,2-trimethylcyclopentyl)propanoate,
but-3-en-1-yl 2-(1,2,2-trimethylcyclopentyl)propanoate,
isobutyl 2-(1,2,2-trimethylcyclopentyl)propanoate,
allyl 2-(1,2,2-trimethylcyclopentyl)propanoate,
methyl 2-(1-methylspiro[4.4]nonan-1-yl)acetate,
methyl 2-(1-methylspiro[4.4]nonan-1-yl)propanoate,
ethyl 2-(1-methylspiro[4.4]nonan-1-yl)acetate,
ethyl 2-(1-methylspiro[4.4]nonan-1-yl)propanoate,
ethyl 2-(1-methyl-2-methylenecyclopentyl)propanoate,
ethyl 2-(4-methylspiro[2.4]heptan-4-yl)propanoate,
ethyl 2-(2-ethyl-1,2-dimethylcyclopentyl)acetate,
ethyl 2-(2-ethyl-1,2-dimethylcyclopentyl)propanoate,
ethyl 2-(1,2-dimethyl-2-propylcyclopentyl)propanoate,
ethyl 2-(1,2,2-trimethylcyclopentyl)acetate,
ethyl 2-(1,2,2-trimethylcyclopentyl)butanoate,
ethyl 2-(1,2,2-trimethylcyclopentyl)pentanoate,
ethyl 2-(1-ethyl-2,2-dimethylcyclopentyl)propanoate,
ethyl 2-(1,2-dimethylcyclopentyl)propanoate,
2-(1,2,2-trimethylcyclopentyl)propanenitrile,
2-(2-ethyl-1,2-dimethylcyclopentyl)acetonitrile,
ethyl 2-(2,2-dimethylcyclopentyl)propanoate,
ethyl 2-(2,2-dimethylcyclohexyl)propanoate,
ethyl 2-(1,2,2-trimethylcyclohexyl)acetate, and
ethyl 2-(1,2,2-trimethylcyclohexyl)propanoate.

\* \* \* \* \*